(12) United States Patent
Cohen et al.

(10) Patent No.: US 8,162,959 B2
(45) Date of Patent: Apr. 24, 2012

(54) SINGLE STAGE HEMOSTASIS CLIPPING DEVICE

(75) Inventors: Adam L. Cohen, Arlington, MA (US); Bryan R. Ogle, Louisville, KY (US); Russell F. Durgin, Attleboro, MA (US); Gregory R. Furnish, Louisville, KY (US); Michael Goldenbogen, Floydsknobs, IN (US); Gary A. Jordan, Litchfield, NH (US); Benjamin E. Morris, Louisville, KY (US); Mark A. Griffin, Louisville, KY (US); William C. Mers Kelly, Crestwood, KY (US); Vasily P. Abramov, Louisville, KY (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 930 days.

(21) Appl. No.: 12/107,559

(22) Filed: Apr. 22, 2008

(65) Prior Publication Data
US 2008/0306491 A1  Dec. 11, 2008

Related U.S. Application Data

(60) Provisional application No. 60/915,806, filed on May 3, 2007.

(51) Int. Cl.
*A61B 17/10* (2006.01)
(52) U.S. Cl. .................................................. 606/142
(58) Field of Classification Search .............. 606/142, 606/151, 213; 227/175.1; 600/104
See application file for complete search history.

(56) References Cited

U.S. PATENT DOCUMENTS

| | | | | |
|---|---|---|---|---|
| 5,015,249 A | * | 5/1991 | Nakao et al. | 606/142 |
| 5,049,153 A | * | 9/1991 | Nakao et al. | 606/151 |
| 5,156,609 A | * | 10/1992 | Nakao et al. | 606/142 |
| 5,222,961 A | * | 6/1993 | Nakao et al. | 606/143 |
| 6,814,742 B2 | * | 11/2004 | Kimura et al. | 606/151 |
| 7,452,327 B2 | * | 11/2008 | Durgin et al. | 600/104 |
| 7,494,461 B2 | * | 2/2009 | Wells et al. | 600/104 |
| 2002/0045909 A1 | * | 4/2002 | Kimura et al. | 606/151 |
| 2005/0070758 A1 | * | 3/2005 | Wells et al. | 600/104 |
| 2005/0107809 A1 | * | 5/2005 | Litscher et al. | 606/142 |
| 2005/0182426 A1 | * | 8/2005 | Adams et al. | 606/142 |
| 2006/0079913 A1 | * | 4/2006 | Whitfield et al. | 606/142 |
| 2009/0043316 A1 | * | 2/2009 | Durgin et al. | 606/142 |

FOREIGN PATENT DOCUMENTS

| | | |
|---|---|---|
| WO | 2005/032381 | 4/2005 |
| WO | 2006/068242 | 6/2006 |

* cited by examiner

*Primary Examiner* — Melanie Tyson
*Assistant Examiner* — Son Dang
(74) *Attorney, Agent, or Firm* — Fay Kaplun & Marcin, LLP

(57) ABSTRACT

A tissue clipping apparatus comprises a clip including a proximal end received within a capsule. The clip includes a clip locking member biased to engage a first locking structure of the capsule to lock the clip in the capsule in a closed configuration. The apparatus also comprises a tension member releasably coupling the clip to a proximal end of the device which, during use, remains accessible to a user. The tension member is coupled to the clip by a joint designed to release when subject to a predetermined load to separate the clip from the device, release of the joint releasing the locking member to engage the first locking structure.

24 Claims, 34 Drawing Sheets

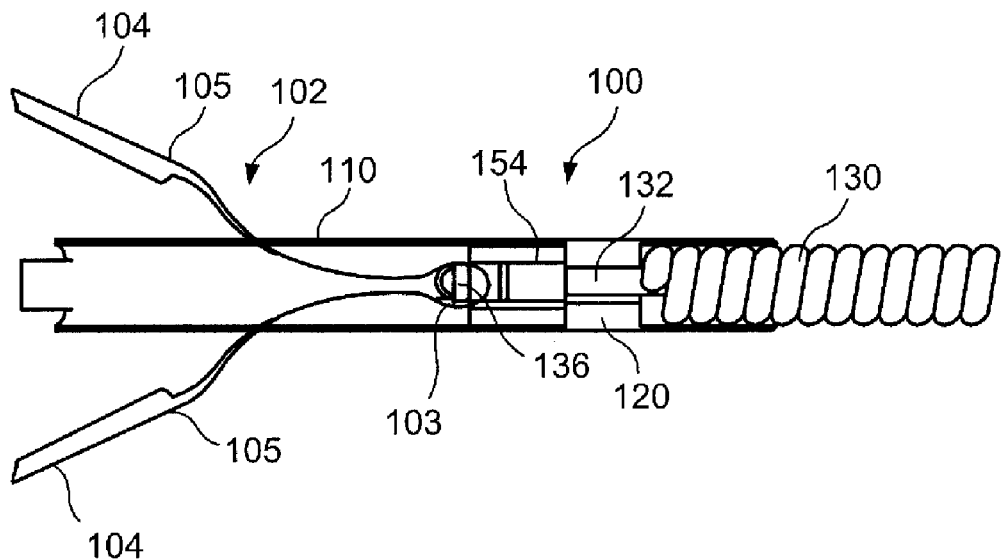
F I G. 1
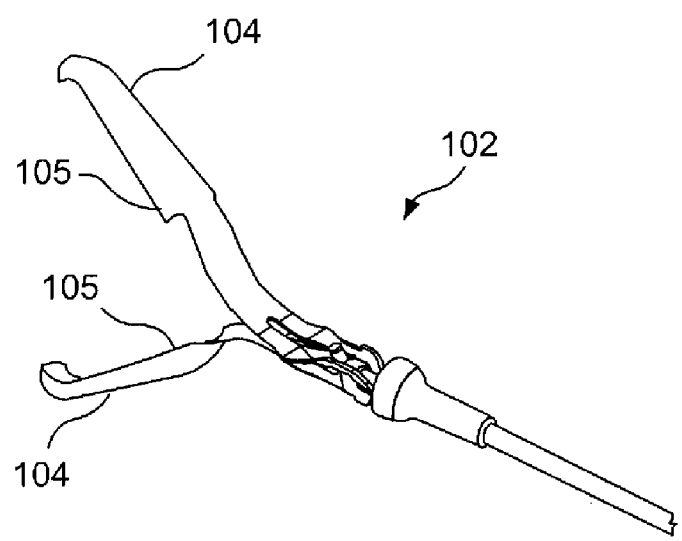
F I G. 1A

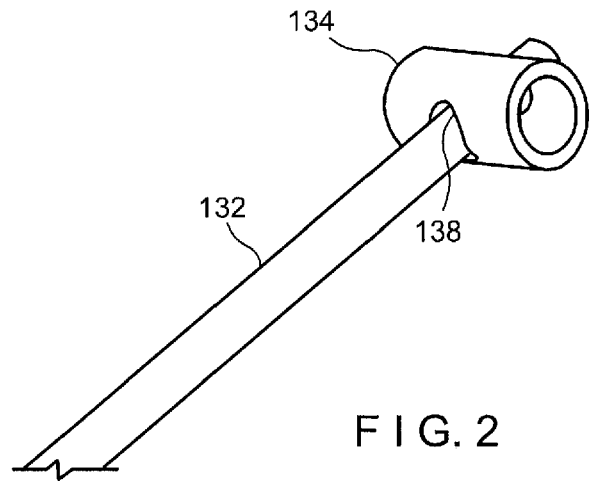
F I G. 2
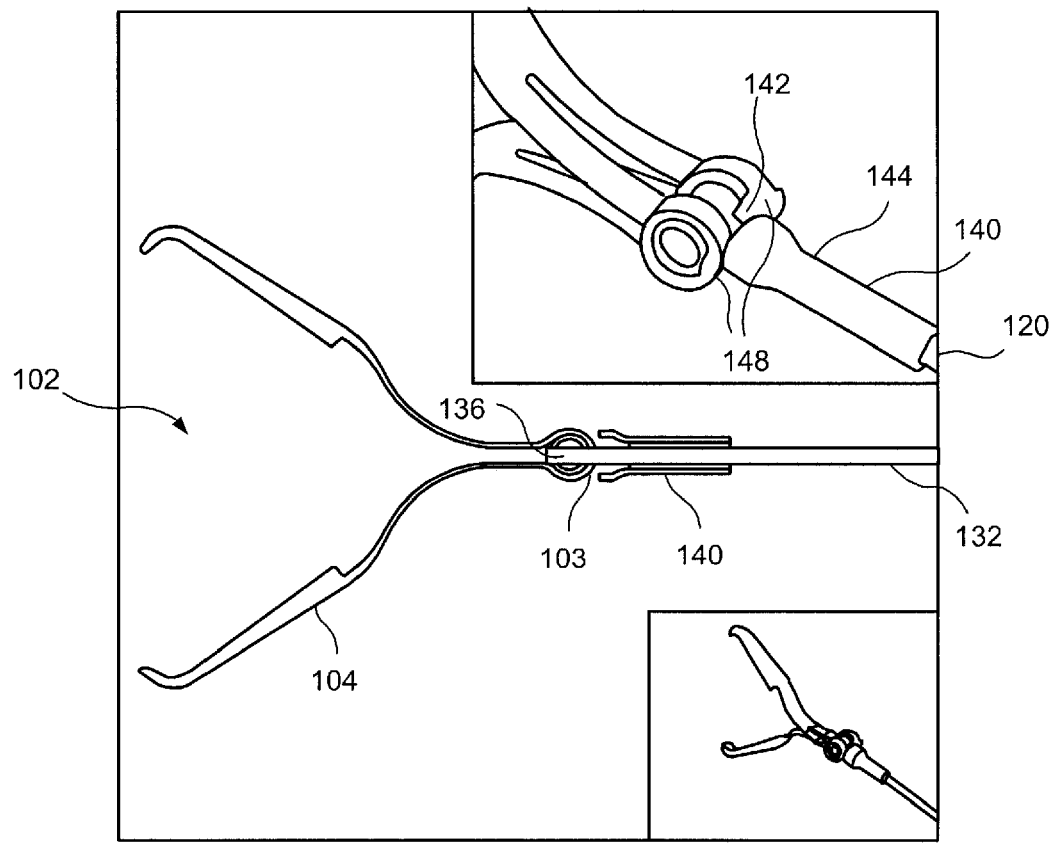
F I G. 3

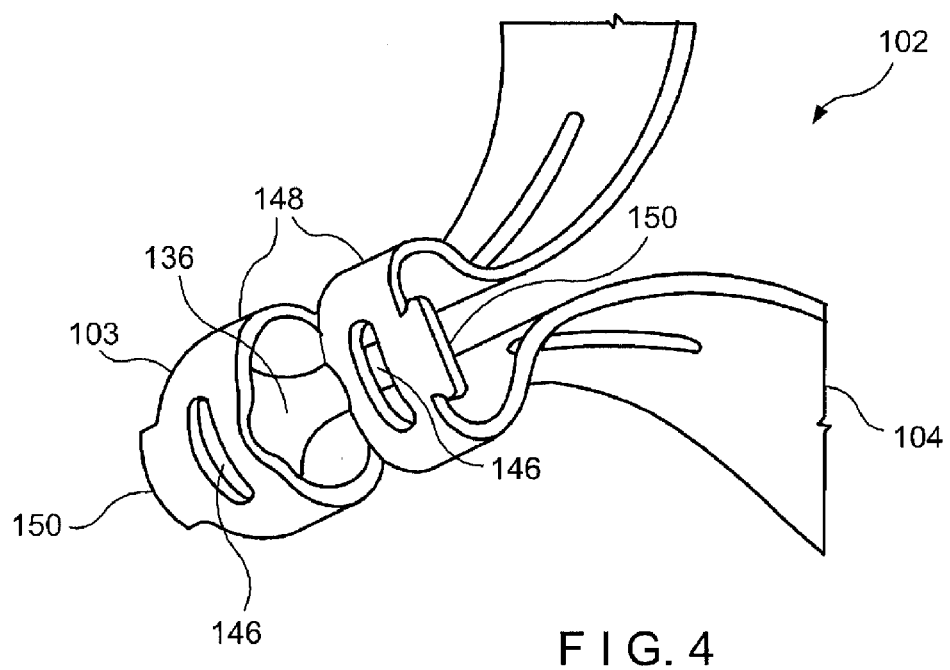
F I G. 4
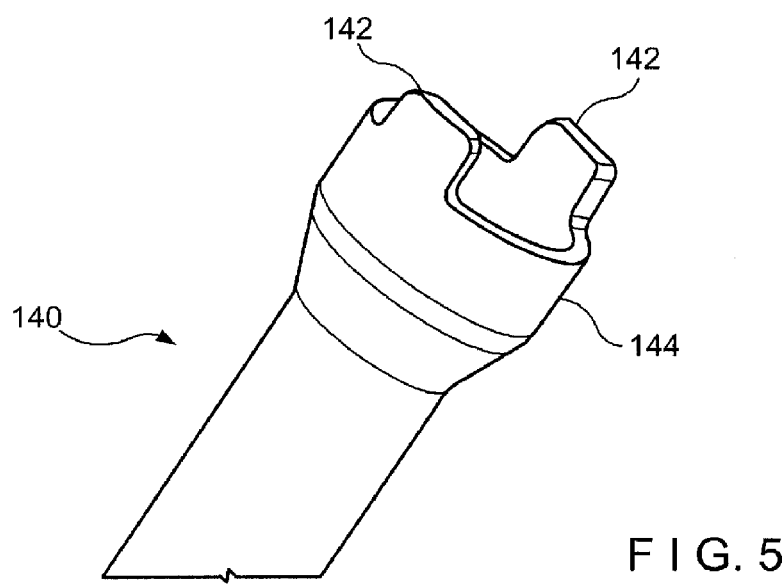
F I G. 5

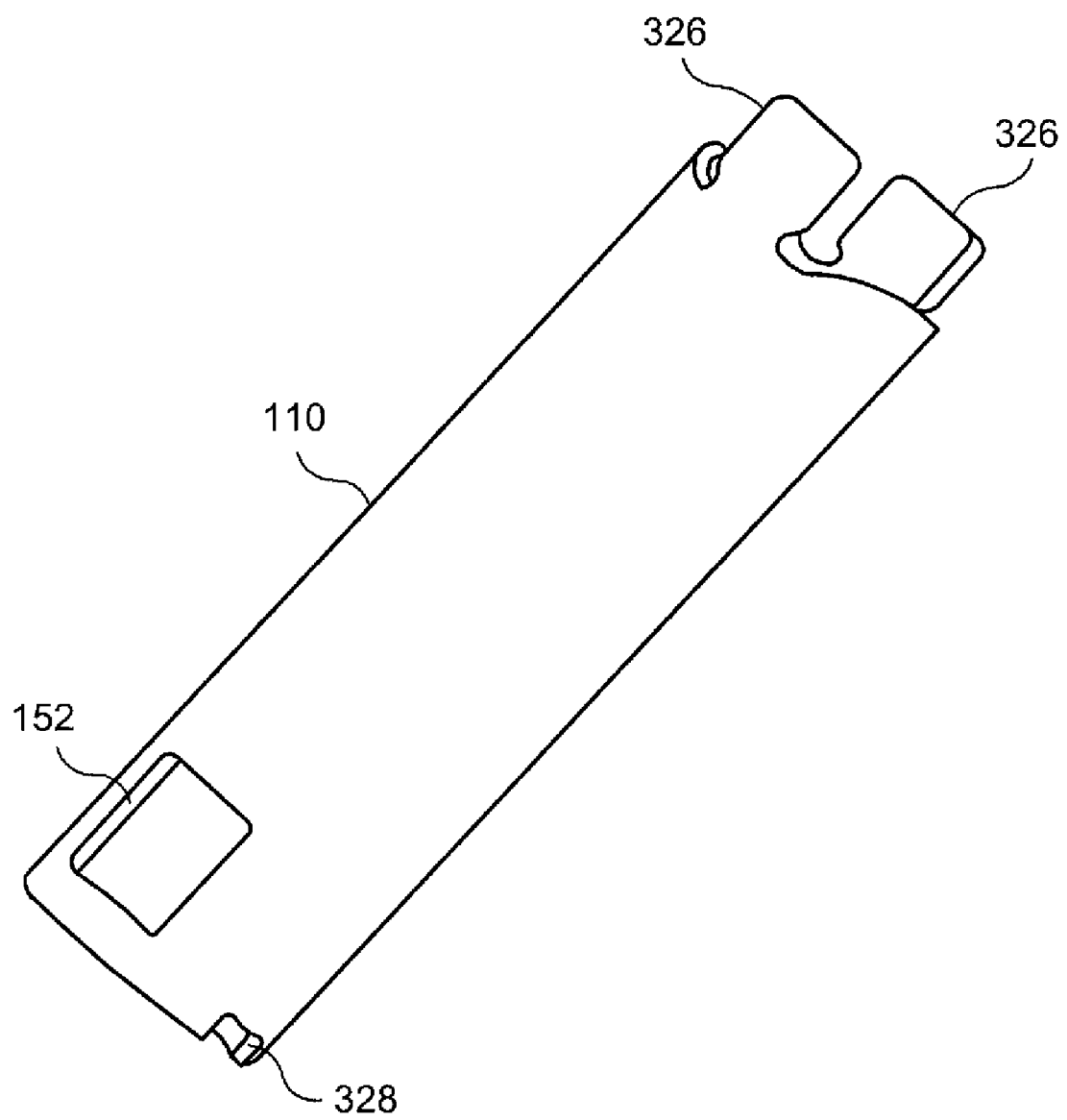
F I G. 6

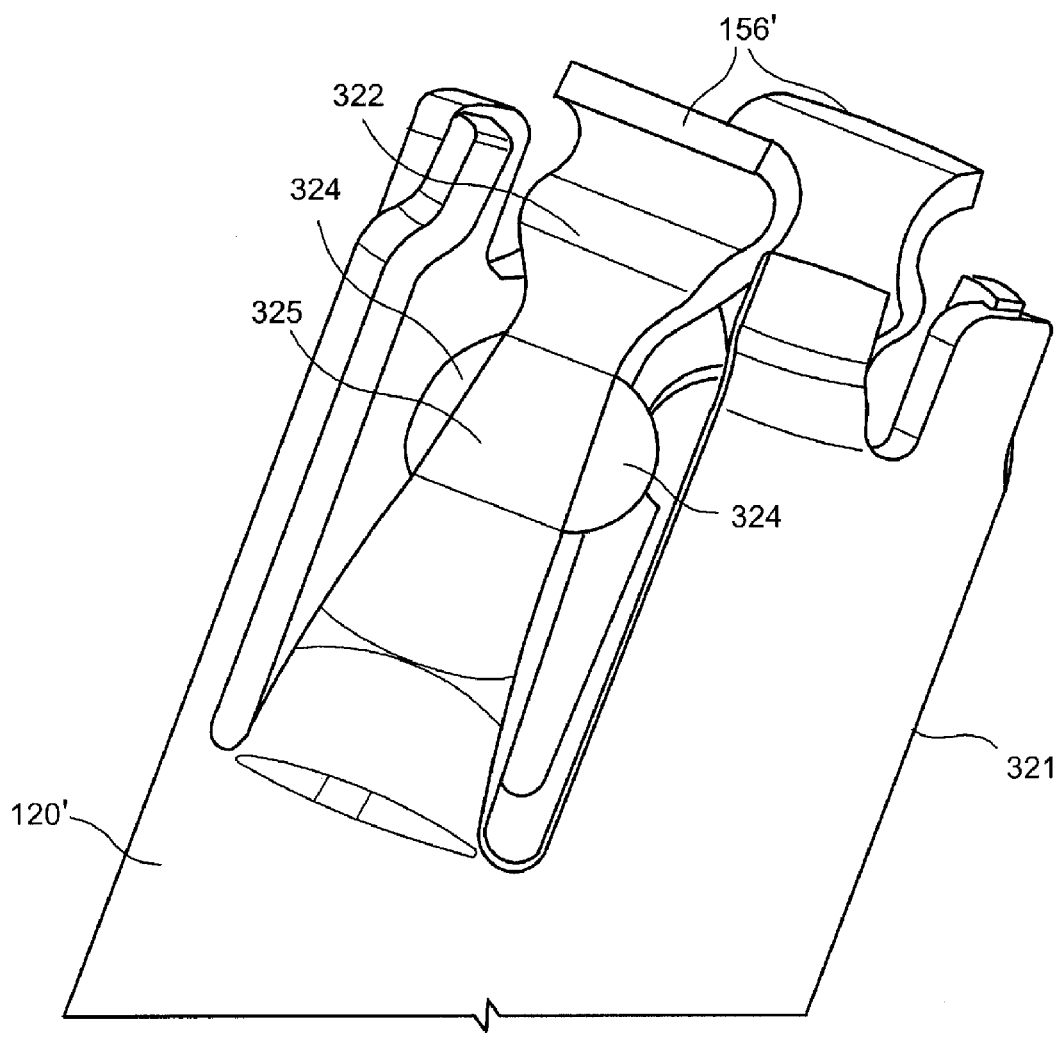
F I G. 9

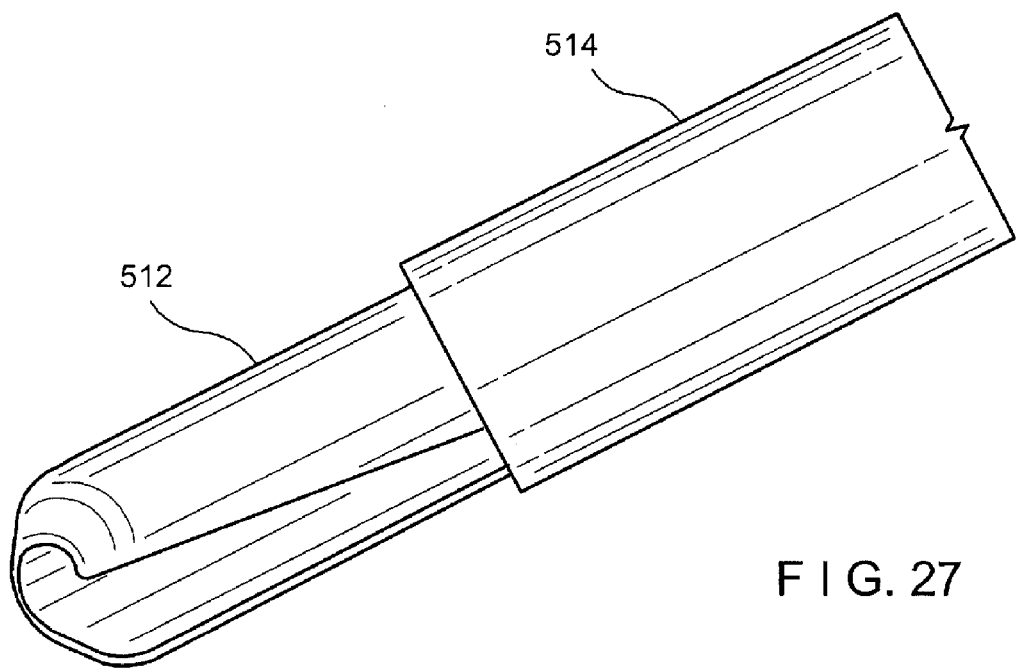
F I G. 27
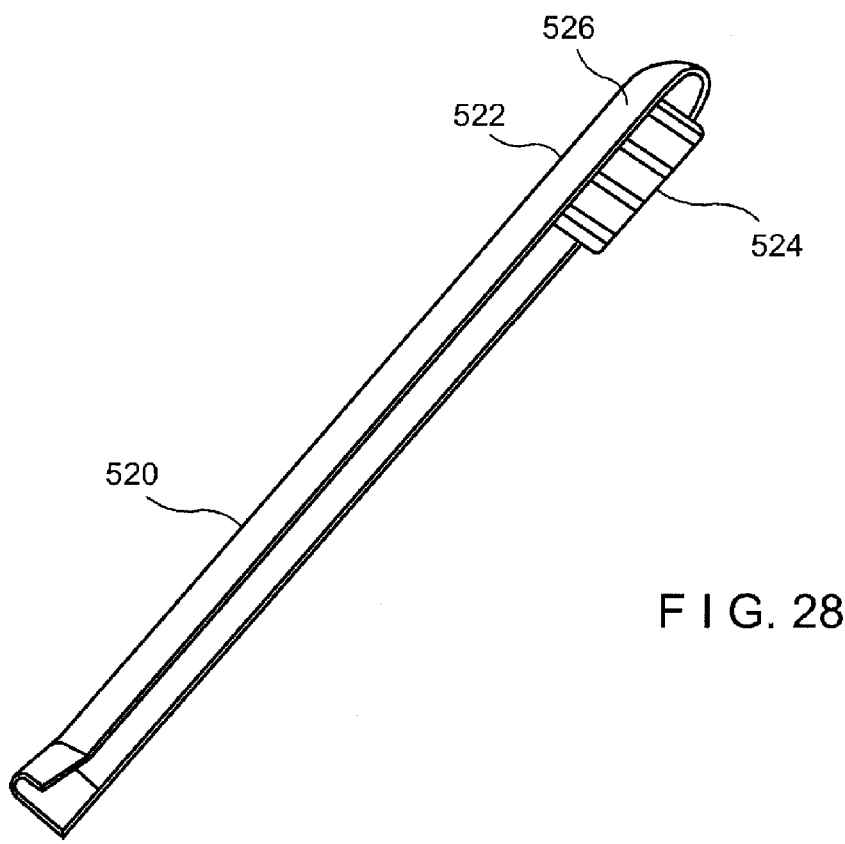
F I G. 28

SECTION AA

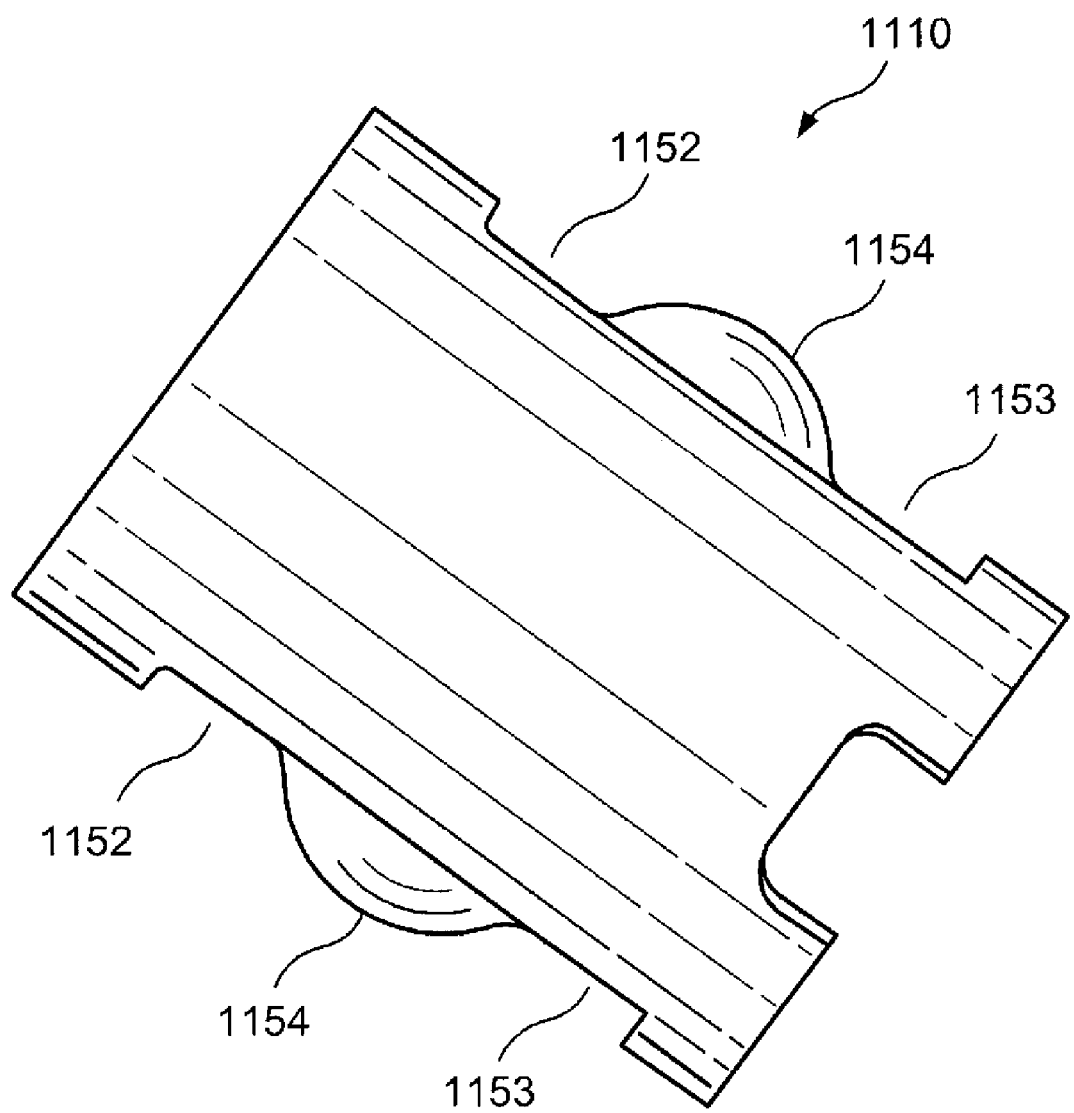
F I G. 32

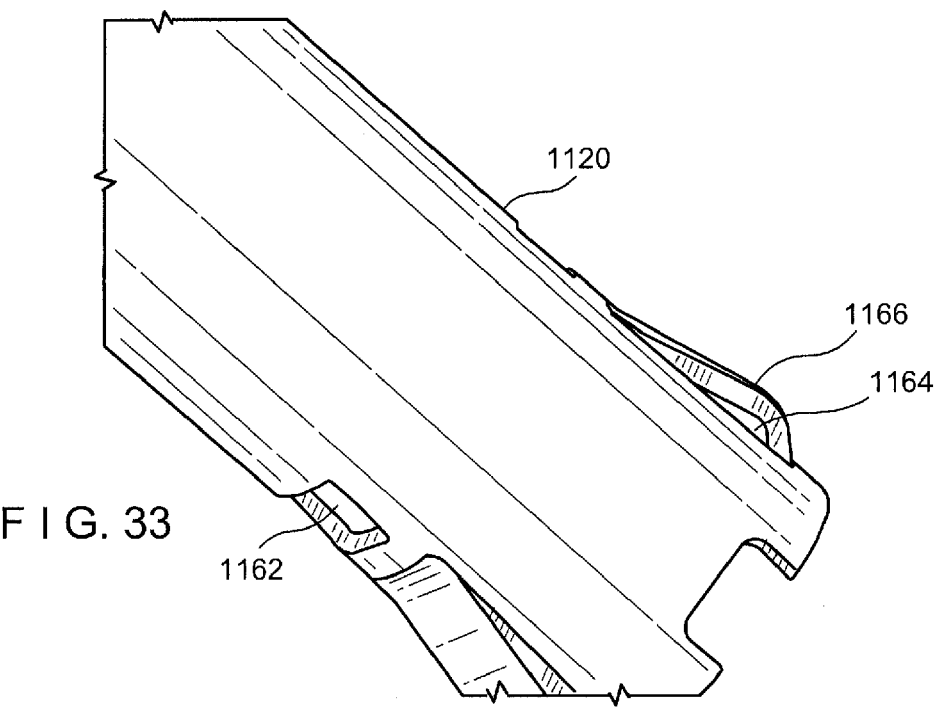
F I G. 33
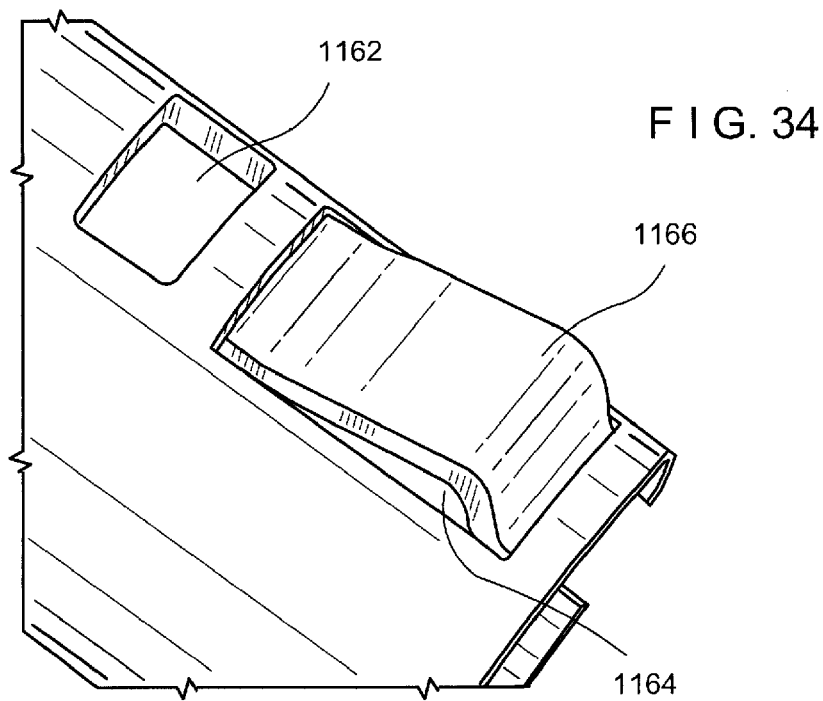
F I G. 34

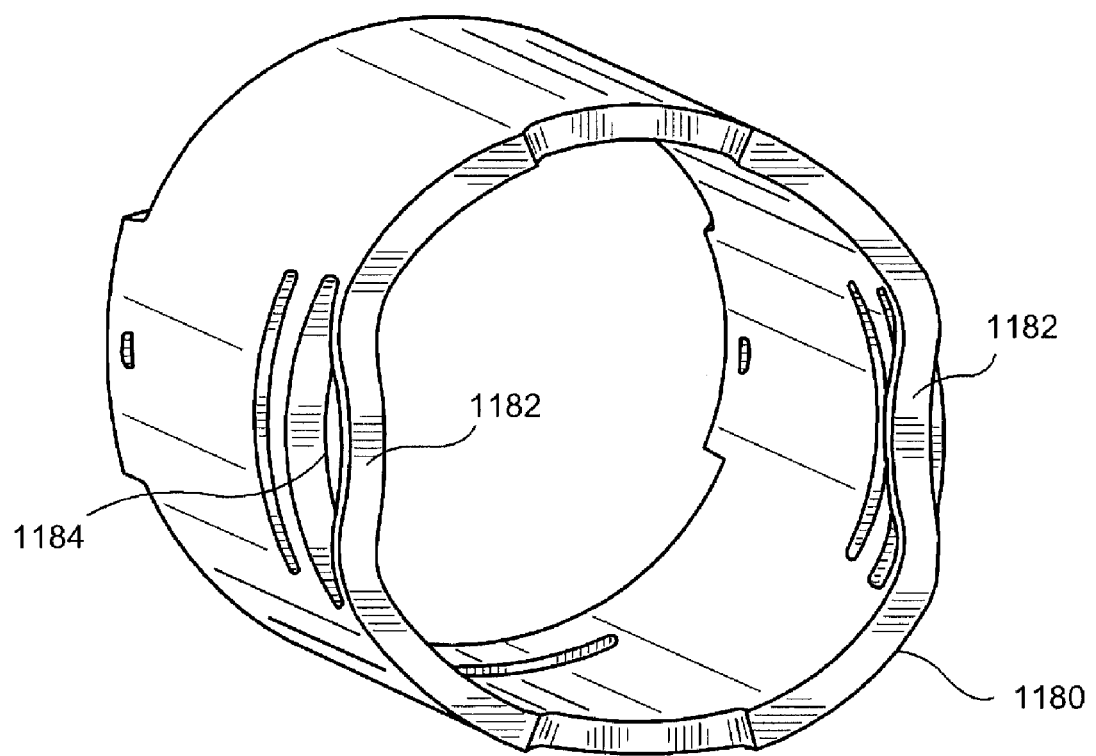
F I G. 37

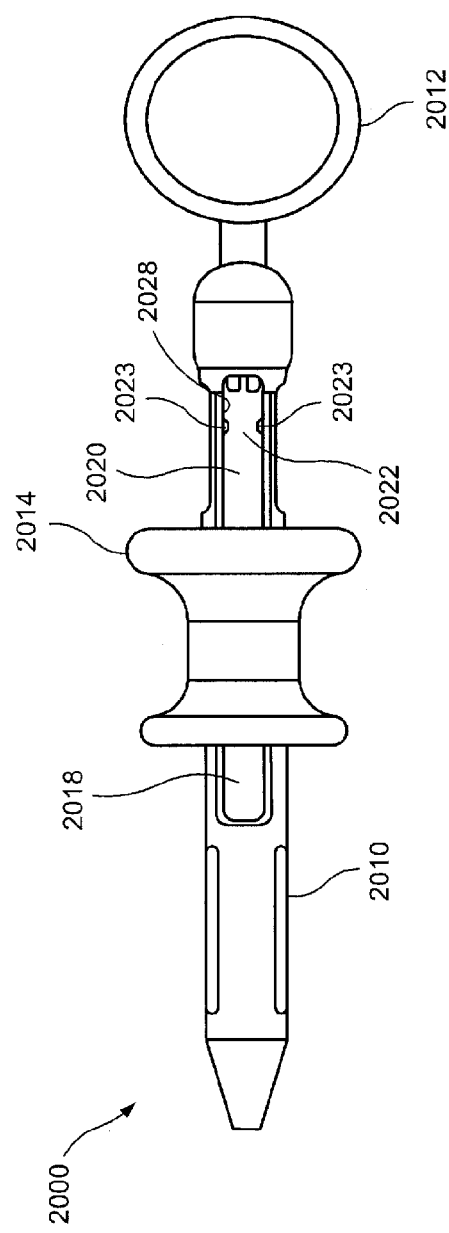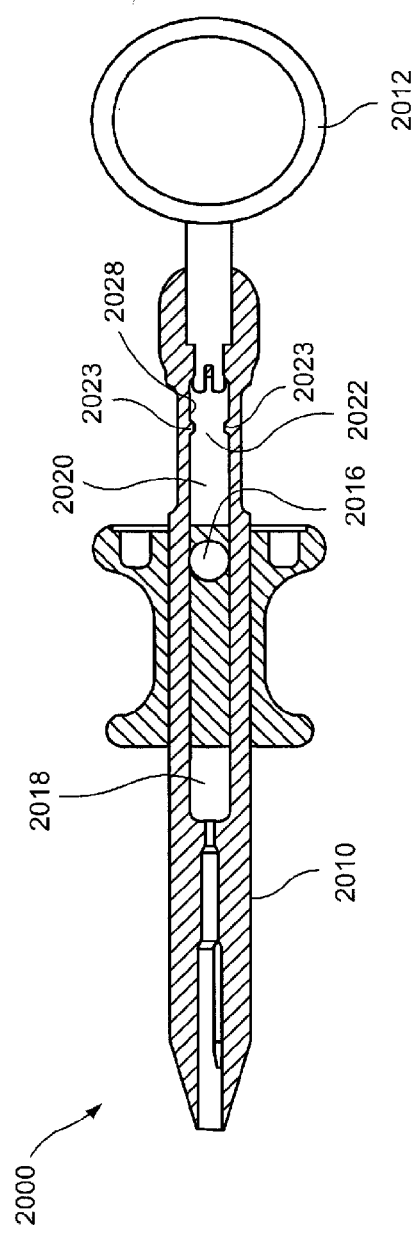

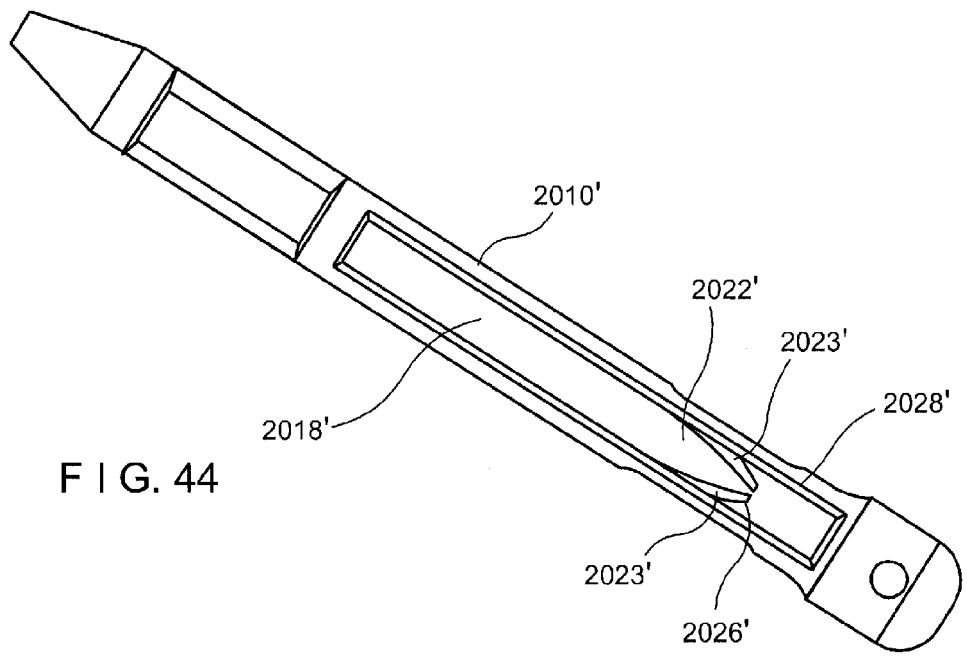
F I G. 44
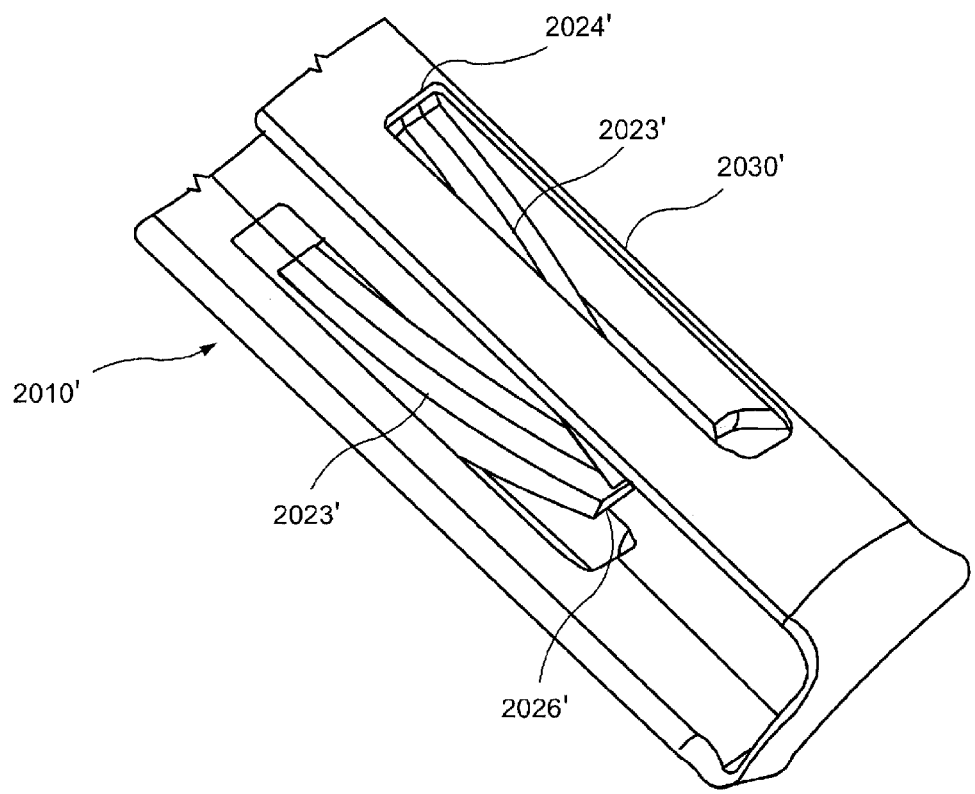
F I G. 45

SINGLE STAGE HEMOSTASIS CLIPPING DEVICE

PRIORITY CLAIM

This application claims the priority to the U.S. Provisional Application Ser. No. 60/915,806, entitled "Single Stage Hemostasis Clipping Device," filed May 3, 2007. The specification of the above-identified application is incorporated herewith by reference.

BACKGROUND

Pathologies of the gastro-intestinal ("GI") system, the biliary tree, the vascular system and other body lumens and hollow organs are commonly treated through endoscopic procedures many of which require active and/or prophylactic hemostasis to reduce internal bleeding. Tools for deploying hemostatic clips via endoscopes are often used to stop internal bleeding by clamping together the edges of wounds or incisions.

In the simplest form, these clips grasp tissue surrounding a wound bringing edges of the wound together to allow natural healing processes to close the wound. Specialized endoscopic clipping devices are used to deliver the clips to desired locations within the body and to position and deploy the clips at the desired locations after which the clip delivery device is withdrawn, leaving the clip within the body.

Endoscopic hemostatic clipping devices are generally designed to reach tissues deep within the body (e.g., within the GI tract, the pulmonary system, the vascular system or other lumens and ducts) via a working lumen of an endoscope. Thus, the dimensions of the clipping device are limited by the dimensions of endoscopic working lumens.

SUMMARY OF THE INVENTION

In one aspect, the present invention is directed to a tissue clipping apparatus comprising a clip including a proximal end received within a capsule, the clip including a clip locking member biased to engage a first locking structure of the capsule to lock the clip in the capsule in a closed configuration and a tension member releasably coupling the clip to a proximal end of the device which, during use, remains outside the body, the tension member being coupled to the clip by a joint designed to fail when subject to a predetermined load in combination with a constraint member coupled to the tension member and releasably connected to the clip, wherein when coupled to the clip, the constraint member maintains the locking member of the clip out of engagement with the first locking structure of the capsule, failure of the control wire detaching the constraint member from the clip.

The present invention is further directed to a clip delivery apparatus comprising a flexible member sized for insertion through a working channel of an endoscope to a target site within a body and a capsule releasably coupled to a distal end of the flexible member including a clip, a proximal end of which is received within the capsule in combination with a tension member extending through the flexible member to a proximal end of the clip and a binding member coupling the tension member to the clip, a connection between the binding member and the tension member yielding when subject to a predetermined load. A constraint member which maintains the clip in an unlocked configuration is coupled to the tension member and releasably connected to the clip so that, when the connection between the binding member and the tension member yields, the constraint member releases from the clip allowing the clip to move to a locked configuration in which the clip is locked closed.

BRIEF DESCRIPTION OF THE DRAWINGS

FIG. 1 is a schematic drawing showing a single piece hemostatic clip according to an embodiment of the present invention;

FIG. 1a is a perspective view a single piece hemostatic clip according to an embodiment of the present invention;

FIG. 2 is a perspective view of a distal tip of a control wire for the clip of FIG. 1;

FIG. 3 is a diagram showing a detail of a single piece clip attached to a control wire;

FIG. 4 is a diagram showing a detail of a proximal end of the single piece clip shown in FIG. 1;

FIG. 5 is a diagram showing a detail of an end of a constraint tube according to the present invention;

FIG. 6 is a diagram showing a capsule for the mechanism of FIG. 1;

FIG. 9 is a diagram showing a second embodiment of a bushing according to the invention;

FIG. 27 is a diagram showing a third embodiment of a channel protector;

FIG. 28 is a diagram showing a fourth embodiment of a channel protector;

FIG. 32 is a side view of an alternate capsule according to an alternate exemplary embodiment for use with the apparatus of FIG. 1;

FIG. 33 is a perspective view of a further alternate capsule for use with the apparatus of FIG. 1;

FIG. 34 is a perspective view of a proximal end of the capsule of FIG. 33;

FIG. 37 is a perspective view of a proximal end of the capsule of FIG. 36;

FIG. 40 is a side view of a handle according to an embodiment of the invention;

FIG. 41 is a cross-sectional side view of the handle of FIG. 40;

FIG. 44 is a side view of a body of a handle according to a further embodiment of the invention;

FIG. 45 is a perspective view of a portion of the handle of FIG. 44;

DETAILED DESCRIPTION

According to the embodiments of the present invention, a single stage mechanical hemostatic clipping device is provided, that is simple to manufacture and to use. The exemplary embodiments of the clipping device improve on the deployment mechanism for both single and two piece hemostatic clips as well as on the mechanism for tip-catheter separation. The embodiments also provide protection of the working channel of the endoscope from sharp edges of the clip deployment device.

Figure 7:
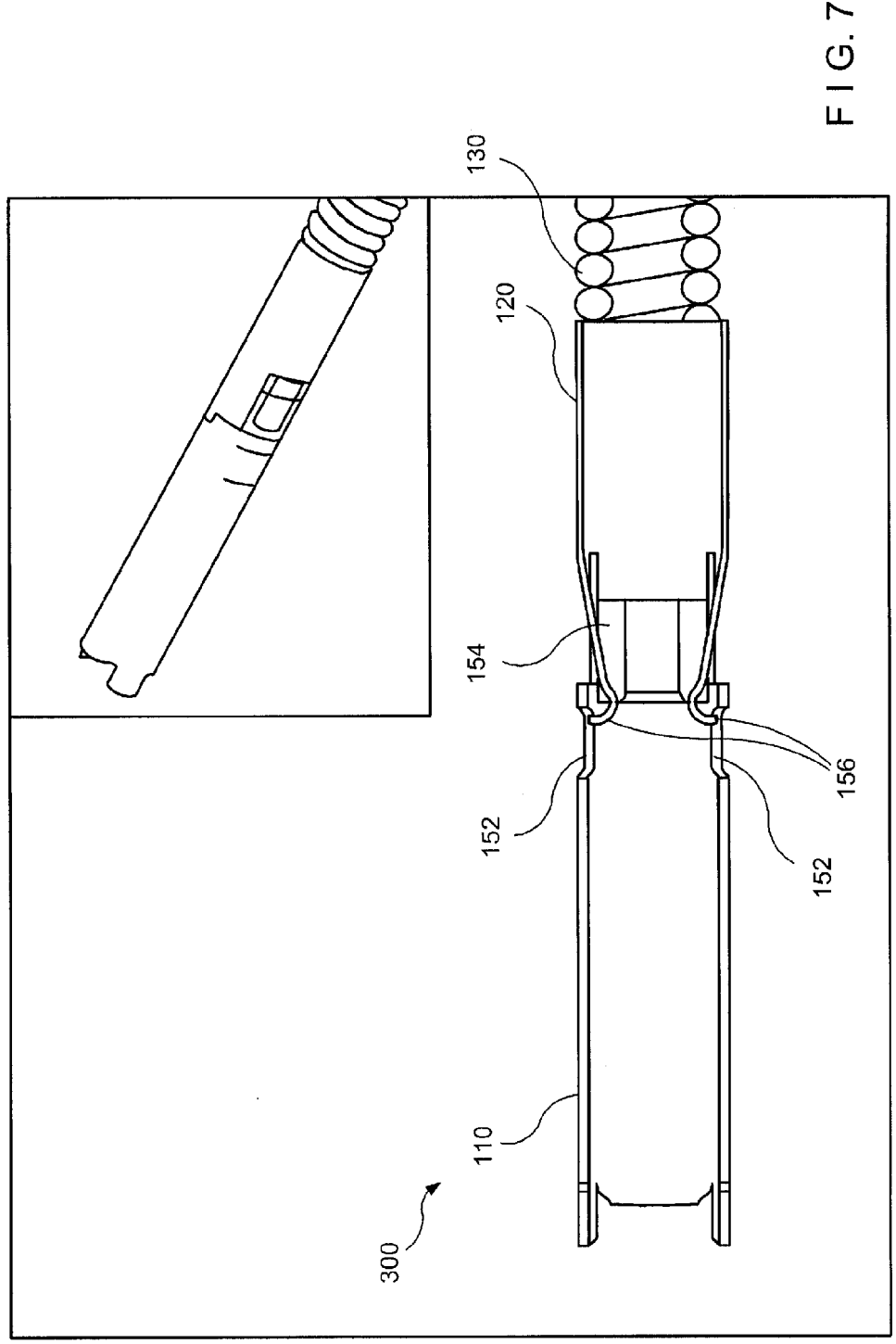
FIG. 7 is a schematic diagram of a bushing and a bushing support for the mechanism of FIG. 1.

As shown in FIGS. 1-7, a clipping device 100 according to an exemplary embodiment of the invention deploys from within a capsule 110 a single piece hemostatic clip 102 including a pair of tissue gripping arms 104 to clamp tissue to, for example, clamp a wound closed to stop bleeding. During insertion, the arms 104 of the clip 102 which are biased toward an open, tissue receiving configuration as shown in FIG. 3, are constrained by the capsule 110 to remain in a closed configuration in which distal ends of the arms 104 are brought together. The capsule 110 is coupled to a bushing 120 which is coupled to a handle (not shown) which remains outside the body via, for example, a flexible member 130 which slidably receives therethrough a control wire 132 which connects the clip 102 to an actuator (not shown) on the handle. As shown in FIGS. 1 and 7, the flexible member 130 may be a coil of wire or any other suitable hollow, flexible structure.

In addition, the clip 102 according to the present invention may be rotated about its axis to increase flexibility in positioning where the flexible member 130 is structured to transmit to its distal end torque applied to its proximal end via, for example, a manually rotatable ring to which the proximal end is coupled. For example, the flexible member 130 may be constructed as an Asahi cable such as the ACTONE cable described in U.S. Pat. No. 6,881,194, to Miyata et al. Rotation applied to the proximal end of such a flexible member 130 in either direction is transmitted to the distal end with minimal wind up, rotating the clip 102 as desired to facilitate more precise placement of the clip 102 over a target portion of tissue. Alternatively, the flexible member 130 may be formed of first and second concentric layers of cable wound about a longitudinal axis of the flexible member 130 so that, rotation in a first direction unwinds the first layer to increase its outer diameter until an outer surface of the first layer frictionally engages an inner surface of the second layer, while rotation of the flexible member 130 in the opposite direction unwinds the second layer until it contacts an inner surface of a lumen within which it is received. An example of a suitable layered cable is described in detail in U.S. Pat. No. 5,932,035 to Koger et al. Those skilled in the art will understand that any suitably thin, flexible member which transmits rotation in both directions without substantially winding up may be used for the flexible member 130. For example, the flexible member 130 may be formed of round wire, flat wire, polymer coated wire with the orientation of the wrap (angle and pitch) selected to permit rotation along an extended length. Such a coil may be formed of a single wire or of a plurality of wires of one or more layers with the layers wrapped in the same or opposite directions and may be braided to constrain the inner or outer diameter of the coil. Furthermore, the wire size of the various layers may be modified to optimize rotation and other physical properties of the flexible member 130. The tension/compression of the flexible member 130 may be stabilized with joints (e.g., weld or solder joints) spaced over the length thereof. Proximal and distal ends of the flexible member 130 will be rigidly coupled to a rotating actuator of a handle and the bushing 120, respectively. The rigid attachment may be formed, for example, via a weld, barb, or adhesive to transmit rotation from the rotating actuator to the clip 102.

As shown in FIGS. 1-3, the clip 102 and the capsule 110 are releasably coupled to proximal portions of the device 100 via a deployment mechanism including a cross bar 134 coupled to a distal end of the control wire 132. The control wire 132 passes through an opening in the proximal end 103 of the clip 102 so that the cross bar 134 is received within a space 136 formed at the proximal end of the clip 102. Proximal movement of the control wire 132 therefore draws the clip 102 proximally. Those skilled in the art will understand that, while the cross bar 134 and the space 136 are substantially cylindrical in this embodiment, they may be of any shape. The cross bar 134 is coupled to the control wire 132 by a joint 138 designed to fail when a desired load is applied to the control wire 132 through, for example, manipulation of the actuator. As the control wire 132 is drawn proximally, the arms 104 are drawn into the capsule 110 so that contact with the capsule 110 draws distal ends of the arms 104 toward one another, compressing any tissue located therebetween. As seen in FIGS. 1 and 1a, distal portions 105 of the arms 104 are wider than proximal portions thereof defining a maximum extent to which the arms 104 may be drawn into the capsule 110. Thus, as the control wire 132 is drawn proximally and the distal ends of the arms 104 approach one another, the force required to compress any tissue gripped thereby applies a load to the control wire 132 via the cross bar 134. After the arms 104 have been drawn into the capsule 110 to the maximum extent, operating the actuator to draw the control wire 132 further proximally applies an increasing amount of force to the control wire 132 and, consequently, to the cross bar 134 (FIG. 2) and the joint 138 (FIG. 2). As would be understood by those skilled in the art, the joint 138 which is designed to fail when subjected to a predetermined load may be formed as a weld or other suitable connection. When the predetermined load is reached and the joint 138 fails, the control wire 132 moves proximally relative to the cross bar 134 which remains trapped within the space 136 by inner walls of the capsule 110. At the same time, movement proximally of the control wire 132 relative to the proximal end of the clip 102 draws a constraint tube 140 as shown in FIG. 3 proximally away from the proximal end of the clip 102 releasing tabs 150 (FIG. 4) of the clip 102 to move laterally outward to engage slots 152 (FIGS. 6 and 7) formed near the proximal end of the capsule 110. This locks the clip 102 closed within the capsule 110, maintaining the clip 102 constrained within the capsule 110 to keep the arms 104 closed over any tissue gripped therebetween. Those skilled in the art will understand that the constraint tube 140 is coupled to the control wire 132 so that there is no relative movement between these components by, for example, welding, crimping or any other suitable method.

More specifically, as shown in FIGS. 3-5, the constraint tube 140 includes a pair of tabs 142 which extend from a flared distal end 144 spaced from one another by a distance selected for alignment with a corresponding pair of slots 146 formed in laterally separated portions 148 of the proximal end of the clip 102. The distance is selected to align with the slots 146 only when the portions 148 are in a laterally constrained configuration as shown in FIG. 3 against a bias of the portions 148 toward a released configuration shown in FIG. 4. Removal of the tabs 142 releases the portions 148 to spread to the released configuration in which the tabs 150 are moved laterally outward to engage corresponding slots 152 (FIG. 6) in the capsule 110 (FIG. 6) locking the clip 102 closed within the capsule 110.

Figure 8:
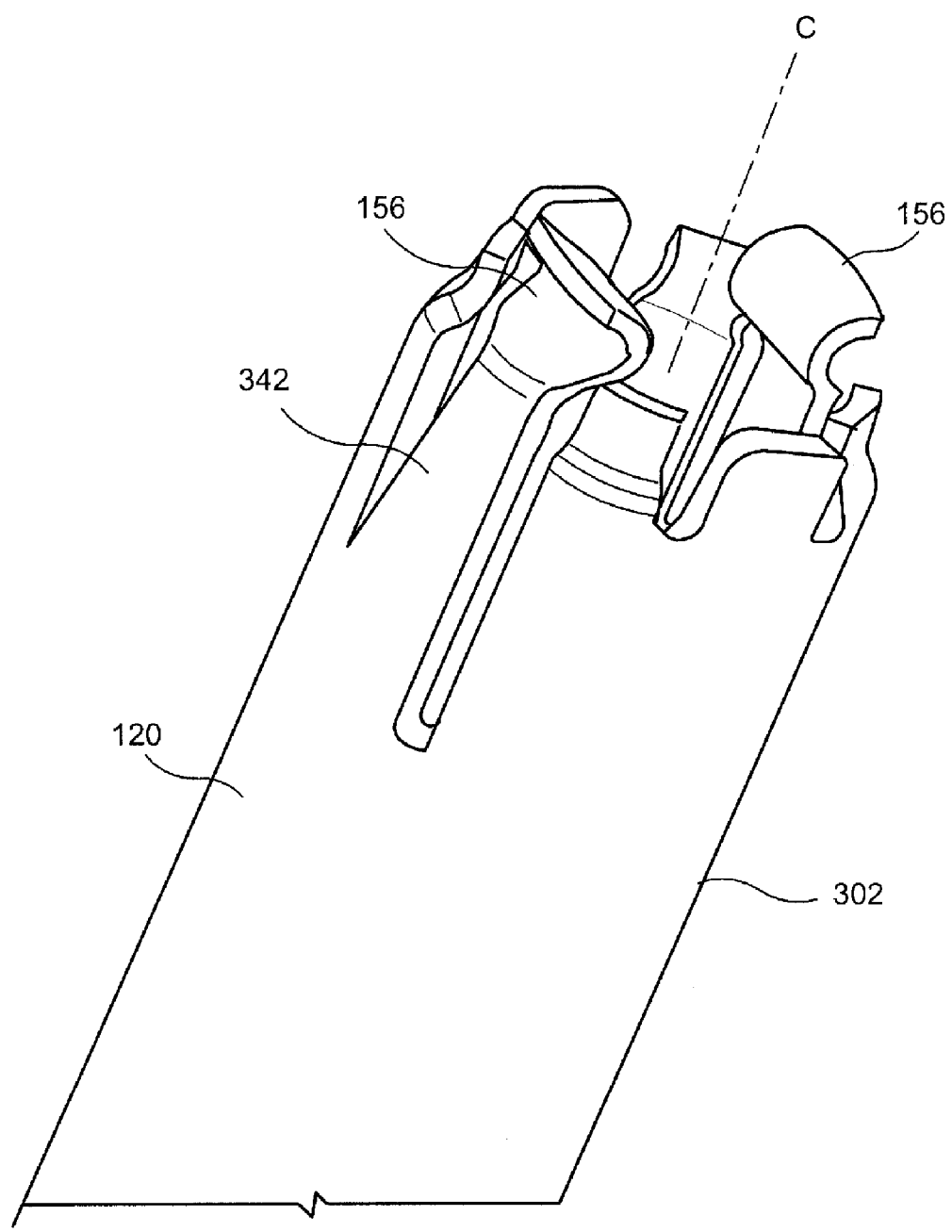
FIG. 8 is a diagram showing a detail of the bushing of FIG. 7.
Figure 12:
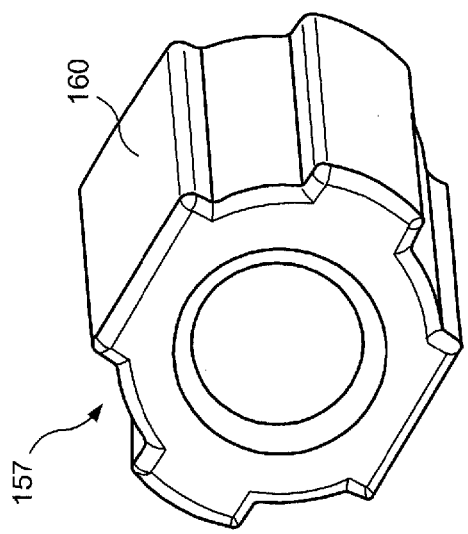
FIG. 12 shows an additional embodiment of a bushing support for the cantilever separation mechanism according to the invention.
Figure 11:
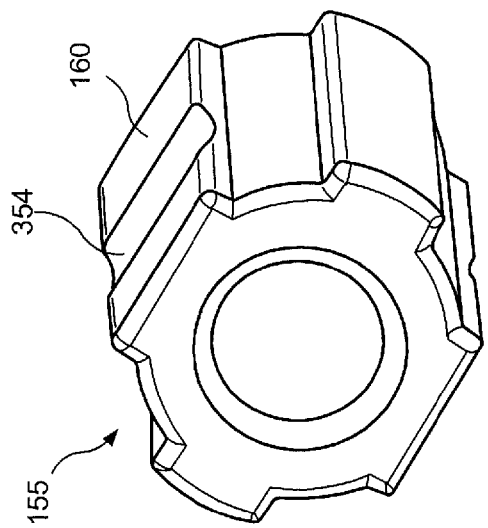
FIG. 11 shows a further embodiment of a bushing support for the cantilever separation mechanism according to the invention.
Figure 10:
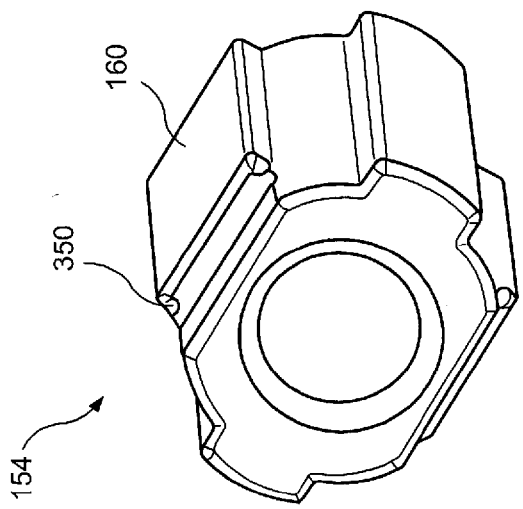
FIG. 10 shows an embodiment of a bushing support for a cantilever separation mechanism according to the invention.
Figure 14:
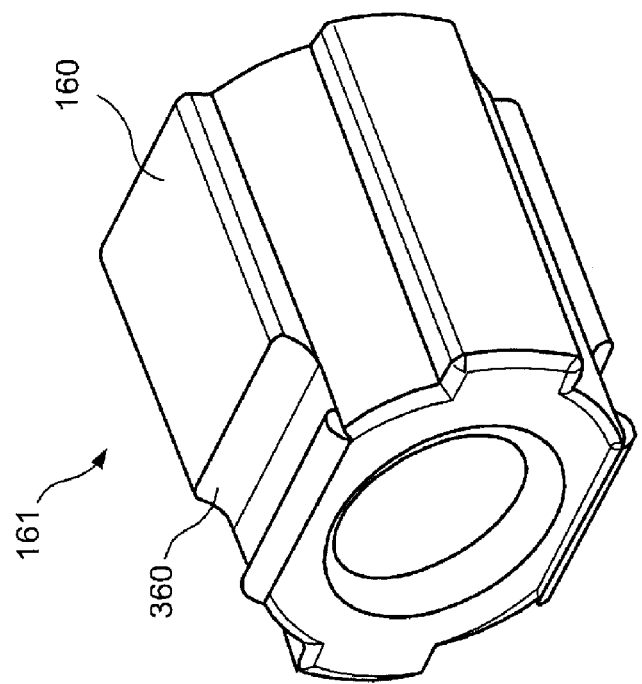
FIG. 14 shows another embodiment of a bushing support for the cantilever separation mechanism according to the invention.
Figure 13:
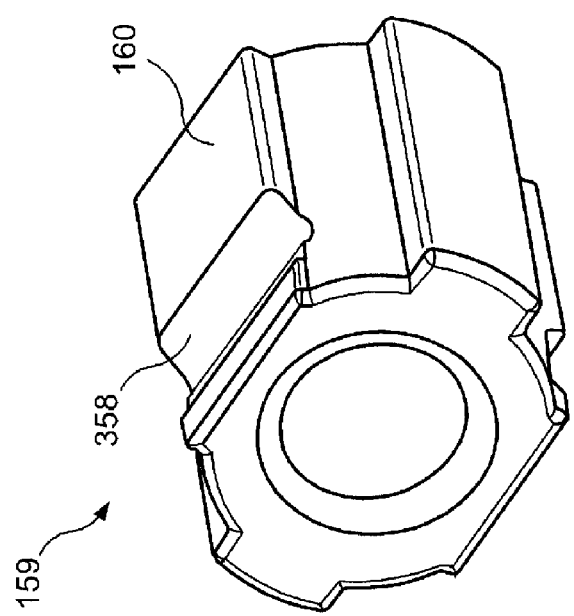
FIG. 13 shows a still further embodiment of a bushing support for the cantilever separation mechanism according to the invention.

As shown in FIGS. 7 and 8, the bushing 120 includes tabs 156 which are moved radially outward when the bushing support 154 is received in the distal end of the bushing 120 to engage the slots 152 in the capsule 110, locking the capsule 110 to the bushing 120. The tabs 156 are biased towards a centerline C of the bushing 120 by, for example, steps during the manufacturing process as would be understood by those skilled in the art. Each of the exemplary bushing supports 154, 155, 157, 159 and 161, shown in FIGS. 10-14, respectively, may be used to form a plug which pushes the tabs 156 radially outward to maintain them locked within the slots 152 of the capsule. Each of the bushing supports 154, 155, 157, 159 and 161 further includes a different arrangement of engaging surfaces 160 which engage radially inner surfaces of the bushing 120 to maintain their position within the bushing 120 and keep the tabs 156 moved outward into engagement with the slots 152. For example, as shown in FIG. 10, both sides of the bushing support 154 include a distal shelf 350 on which a distal end of the corresponding tab 156 is received. The bushing support 155 of FIG. 11 includes a groove 354 in the surface 160 within which radially inward projections of the tabs 156 are received while the bushing support 157 of FIG. 12 contacts the tabs 156 on a substantially smooth surface. The bushing support 159 of FIG. 13 includes pockets 358 formed in the surface 160 within which radially inward projections of the tabs 156 are received while the bushing support 161 of FIG. 14 includes an undercut recess 360 in the surface 160. Those skilled in the art will understand that the geometry of the contact between the bushing support and the tabs 156 may be varied in a range of ways to achieve a desired level of force required to dislodge the bushing support from the bushing 120.

In other respects the bushing supports 154, 155, 157, 159 and 161 operate substantially identically. Thus, although further discussion of the bushing supports will focus on the bushing support 154, those skilled in the art will understand that this will be equally applicable to the additional bushing supports 155, 157, 159 and 161 unless specifically disclaimed. The bushing supports 154, 155, 157, 159 and 161 are preferably formed of any biocompatible polymer, metal or acrylic and may include surface features designed to interact with corresponding structures of the tabs 156. The capsule 110, the clip 102 and the bushing 120 are preferably formed of a metal or other bio-compatible material sufficiently strong and flexible that the desired clipping force (e.g., sufficient to achieve hemostasis) may be achieved and that the bias of the various tabs is sufficient to maintain the parts locked together. In addition, it may be desired to form the parts remaining within the body upon completion of the procedure (clip 102, capsule 110 and cross bar 134) of MRI compatible materials such as lead free metals (e.g., Titanium, Nitinol).

Referring back to FIGS. 1-6, the constraint tube 140 moves proximally toward a bushing support 154 received within a distal end of the bushing 120 after the failure of the joint 138 and the locking of the tabs 150 into the slots 152. A diameter of the flared end 144 of the constraint tube 140 is selected to be greater than a diameter of a lumen 162 of the bushing support 154 so that, the flared end 144 abuts a distal end of the bushing support 154 pushing the bushing support 154 out of its position in the distal end of the bushing 120 and releasing the tabs 156 to move radially inward under their bias out of engagement with the slots 152. This decouples the capsule 110 from the bushing 120 leaving at the target site the clip 102 clamped on the tissue and the capsule 110 coupled thereto. The bushing 120 and the remainder of the device 100 may then be withdrawn from the body.

As shown in FIG. 6, the capsule 110 comprises two tabs 326 disposed at the distal end that are bent at approximately 90° inward toward a centerline of the capsule 110. The tabs 326 hold the clip 102 in position until deployment preventing the clip from rotating about a longitudinal axis of the capsule 110, limiting the extent of travel of the clip 102 distally relative to the capsule 110 and acting as cams forcing the arms 104 open as the clip 102 is pushed distally from the end of the capsule 110. Because the tabs 326 are bent substantially perpendicular to the longitudinal axis of the capsule 110, the tabs 326 extend across the distal opening of the capsule 110 defining a distal-most position of the clip 102. That is, as the clip 102 is advanced distally, the arms of the clip 102 are spread at a wider and wider angle and the tabs 326 are received between portions of the arms which, in the resting position are positioned increasingly closer together. Eventually the portion of the clip 102 contacting the tabs 326 cannot spread greater than the width of the tabs 326 preventing further distal motion of the clip 102. Alternatively, the tabs may eventually contact the cross bar 134. In either case, the tabs 326 define a distal-most position for the clip 102. In addition, the proximal end of the capsule 110 comprises two or more grooves 328 facilitating the maintenance of a desired alignment between the capsule 110 and the bushing 120.

The bushing 120 is preferably configured to meet specific requirements. For example, as shown in FIG. 8, the tabs 156 of the bushing 120 are coupled to a cylindrical body 302 of the bushing 120 via a flat transition 342 to minimize yielding due to stresses applied thereto. In this exemplary embodiment, there is only a frictional interface between the inside of the tabs 156 and the engaging surfaces of the bushing support. As shown in FIG. 9, tabs 156' of a bushing 120' according to an alternate embodiment of the invention are coupled to the cylindrical body 321 via a curved section 325. Bent ears 324 are also included along the tabs 156' to increase the engagement surface between the bushing 120' and the bushing support.

Figure 15:
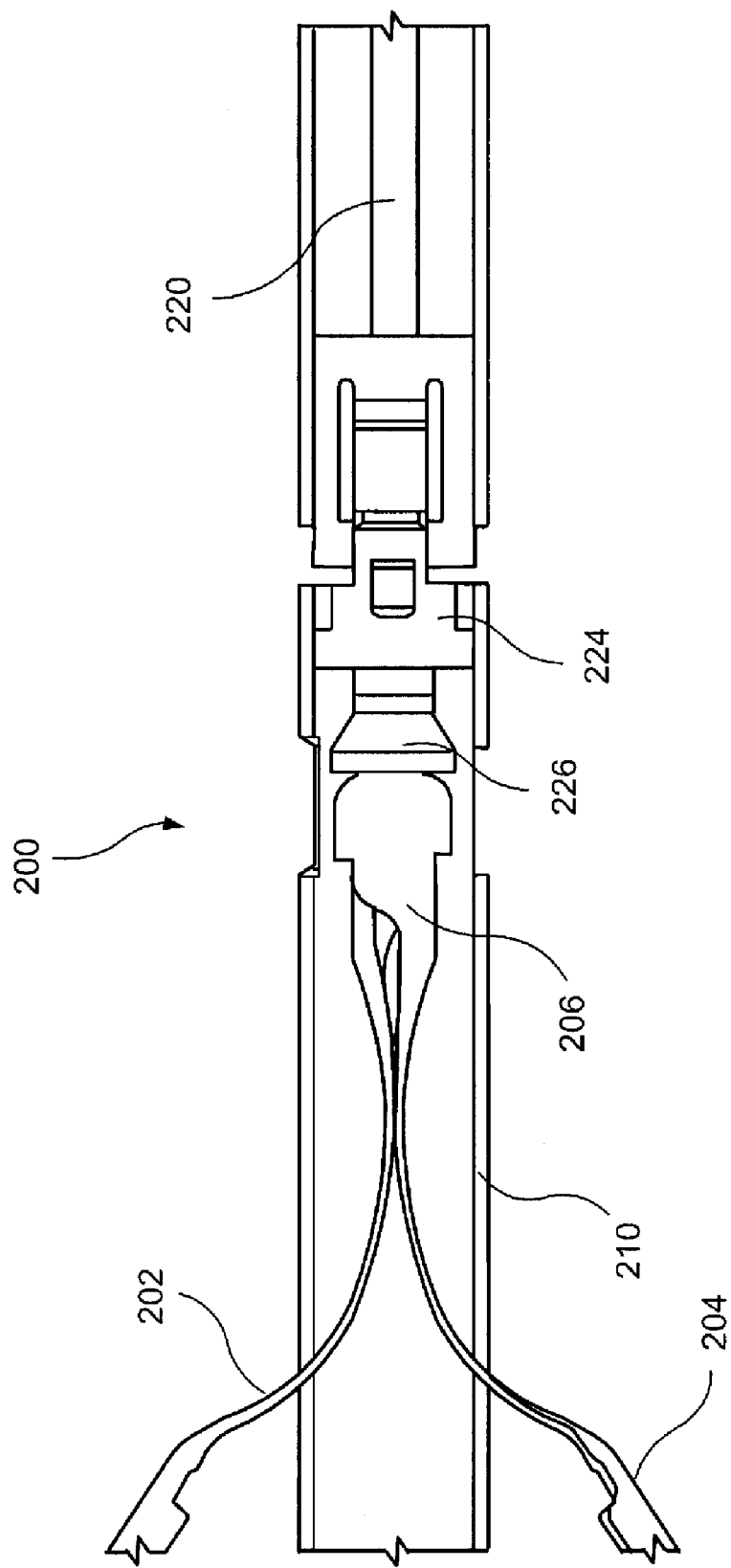
FIG. 15 is a schematic drawing showing a two piece hemostatic clip according to an alternative embodiment of the present invention.
Figure 16A:
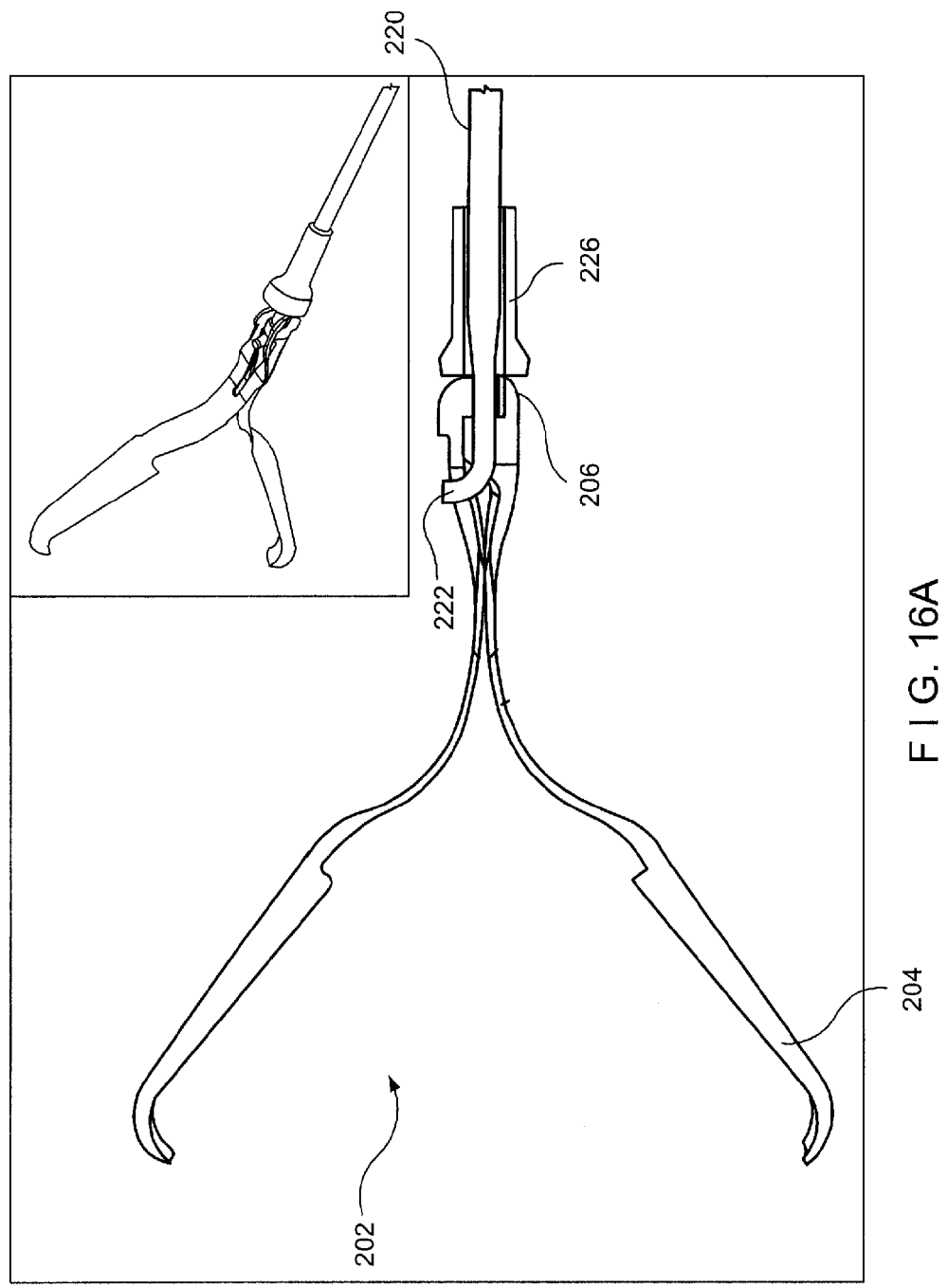
FIG. 16a is a cross sectional schematic diagram showing a connection of the clip of FIG. 15 with a control wire.
Figure 16B:
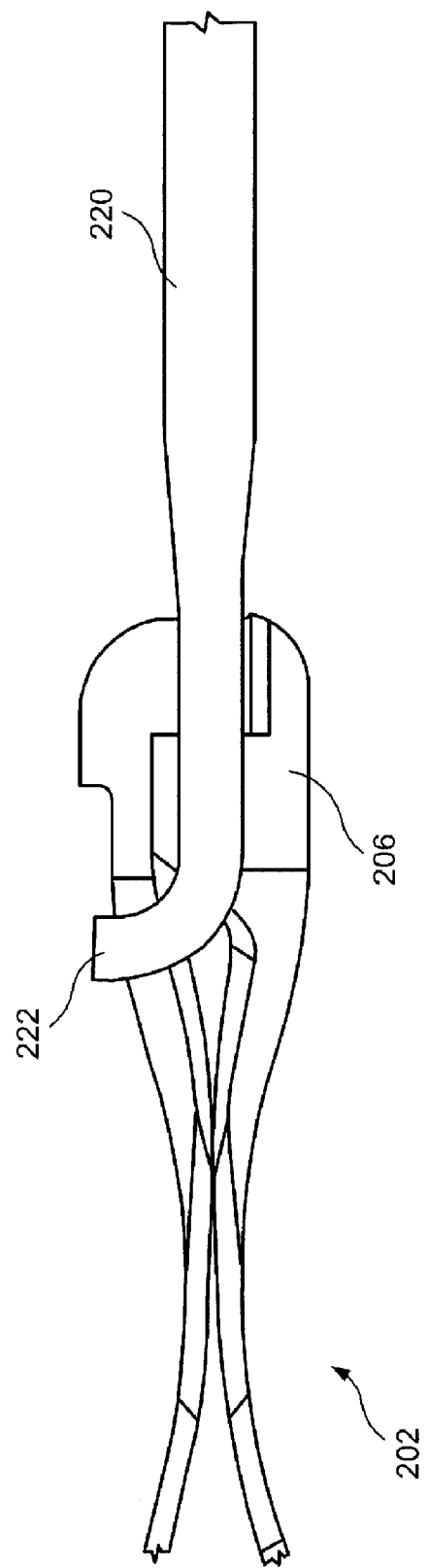
FIG. 16b is a further cross sectional schematic diagram showing a connection of the clip of FIG. 15 with a control wire.
Figure 16C:
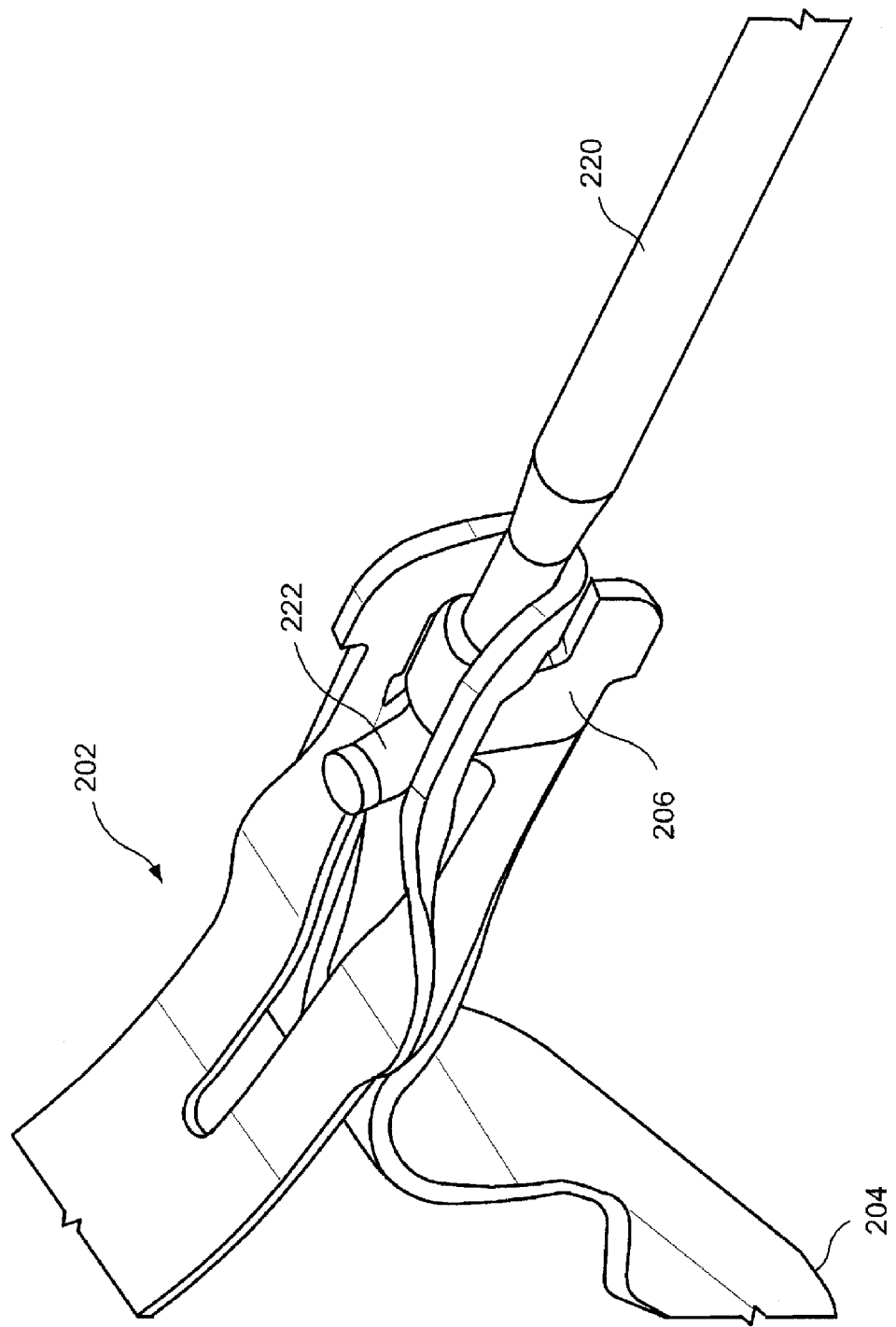
FIG. 16c is a further cross sectional schematic diagram showing a connection of the clip of FIG. 15 with a control wire.

FIGS. 15-16c show a two piece hemostatic clip 202 comprising a bent wire constrained before deployment which unbends when released during deployment. As shown in FIG. 15, the two piece hemostatic clip 202 comprises a pair of arms 204, proximal ends of which interlock with one another with a control wire 220 passing therethrough and latching onto each of the arms 204. The proximal ends of the clip 202 form tabs 206 which are biased outward toward so that, when the control wire 220 is pulled away from the clip 202 and the proximal ends thereof are released, the tabs 206 are moved radially outward by this bias to engage slots in the capsule 210 as described above in regard to the clip of FIG. 1. As the control wire 220 is pulled free of the clip 202, a plunger 226 which is coupled to the control wire 220 is moved proximally in the same manner as the constraint tube of the device of FIG. 1 until it contacts and dislodges a bushing support 224 or, in an alternative configuration, pull an interlock tube into the bushing 221 (as described in more detail below) freeing the capsule 210 from the bushing 221 as described above in more detail. As would be understood by those skilled in the art, the plunger 226 may, for example, be welded or crimped to the control wire 220 or coupled thereto in any other suitable manner. The plunger 226 may push the clip 202 forward when opening the clip 202.

As shown in FIG. 16a-16c, deployment of the two piece clip 202 is substantially similar to that of the clip 102 except that the breakable joint 138 of FIG. 2 is replaced by a bent distal portion 222 of the control wire 220 which straightens when subjected to a predetermined load to allow relative movement between the control wire 220 and the proximal end of the clip 202, freeing tabs of the clip 202 to expand laterally and lock into corresponding slots on a capsule 210 in the same manner described above for the clip 102. Specifically, the bent distal portion 222 of the control wire 220 is straightened and fed through an opening of the clip 202. Once the distal portion 222 is through the opening, the distal portion 222 is allowed to bend to its resting state.

As described above in regard to the clip 202, a load may be applied to the control wire 220 by, for example, actuating a manual deployment control to pull the control wire 220 proximally drawing the clip 202 into the capsule 210 until wider portions of arms 204 of the clip 202 engage the capsule 210 preventing further proximal movement of the clip 202 relative to the capsule 210. Pulling the control wire 220 further proximally applies tension to the control wire 220 which unbends (i.e., straightens) the bent distal portion 222 of the control wire 220 releasing the control wire 220 from the proximal end of the clip 202 and ultimately releasing the clip 202 to lock into a capsule 210 as described above.

Figure 17:
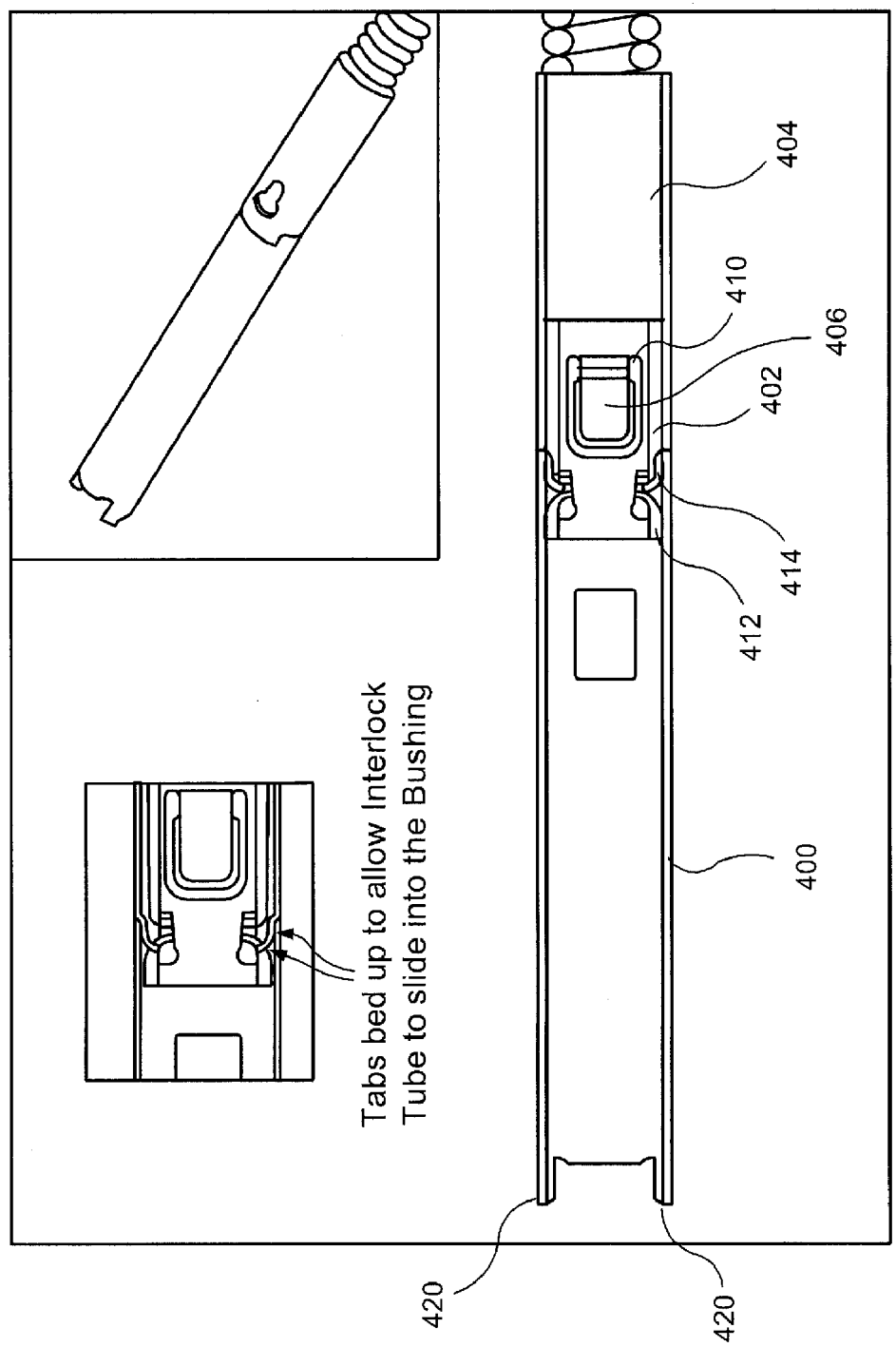
FIG. 17 shows an exemplary embodiment of a connection mechanism for the interlock tube according to the invention.

FIG. 17 shows a tip catheter separation mechanism comprising a capsule 400, an interlock tube 402 and a bushing 404. This embodiment provides for a more positive interference between the capsule 400 and the interlock tube 402, as well as between the interlock tube 402 and the bushing 404. The interlock tube 402 comprises spring tabs 406 that lock into windows 410 of the bushing 404 when the two components are connected. The proximal end of the capsule 400 comprises tabs 412 which, during the assembly of the device, are bent into the windows 414. When the deployment mechanism is activated, a frangible link (e.g., the bent distal portion 222 of the control wire 220) is released, so that the control wire 220 and the constraint tube 130 connected thereto are pulled proximally through the capsule/bushing sub-assembly. As the constraint tube 130 passes through the capsule 400 and the bushing 404, it forces the interlock tube 402 into the bushing 404 pulling the tabs 412 of the capsule 400 proximally and straightening them in the process. This separates the bushing 404 from the capsule 400 while similar mechanisms to those described above lock the clip to clamp over the selected portion of tissue. The exemplary capsule 400 comprises two tabs 420 disposed at the distal end which bend approximately 90 degrees inward to hold the hemostatic clip in position and to force the clip arms open during deployment.

Figure 18:
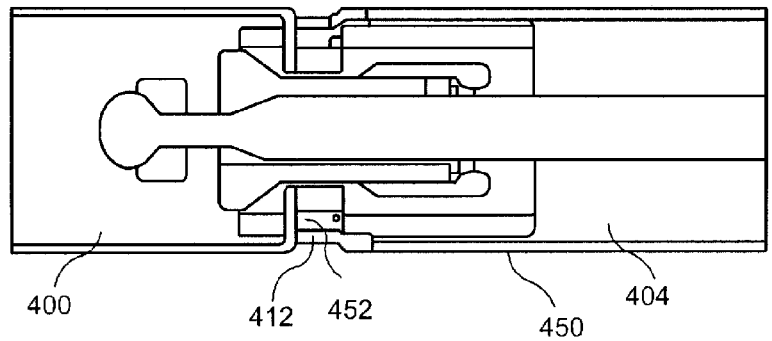
FIG. 18 shows a further exemplary embodiment of a connection mechanism for the interlock tube according to the invention.

The portions of the interlock tube that bend the proximal tabs 412 of the capsule 400 may have any of a variety of different configurations. For example, as shown in FIG. 18, the interlock tube 450 located between the capsule 400 and the bushing 404 may comprise a substantially square pocket 452 receiving the proximal capsule tabs 412. When the bent distal portion 222 unbends, the plunger 226 moves proximally with the control wire 220 until it interfaces the interlock tube, thereby moving the plunger 226 into the bushing 404.

Figure 19:
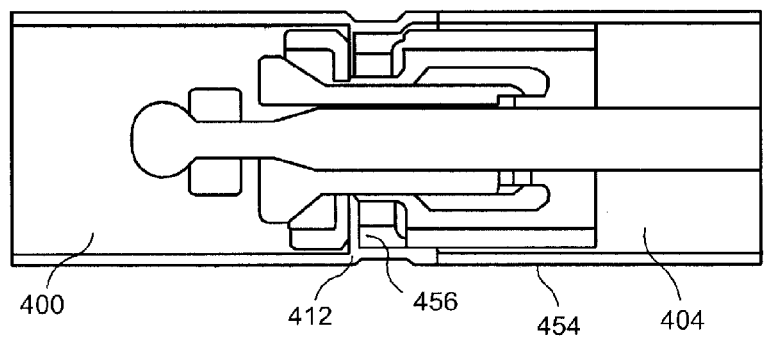
FIG. 19 shows an additional exemplary embodiment of a connection mechanism for the interlock tube according to the invention.
Figure 20:
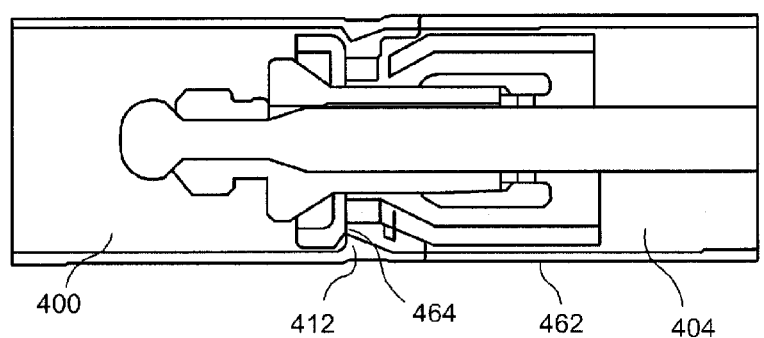
FIG. 20 is a diagram showing a first exemplary embodiment of a tab configuration for a capsule according to the invention.
Figure 23:
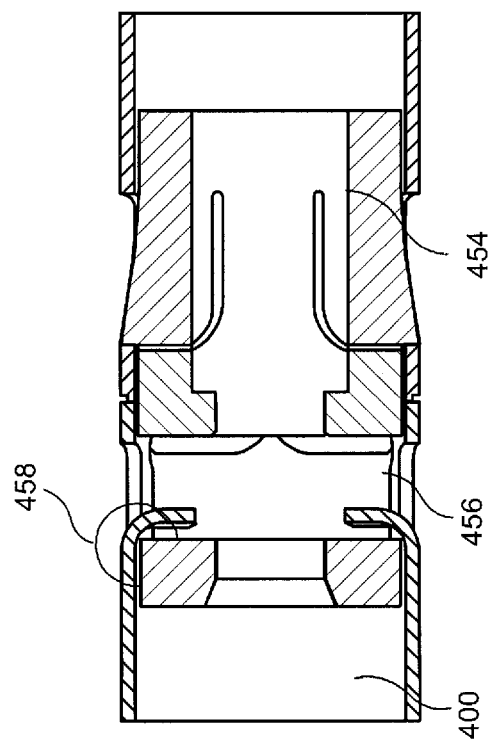
FIG. 23 is a diagram showing a detail of a first embodiment of the interlock tube shown in FIG. 19.
Figure 24:
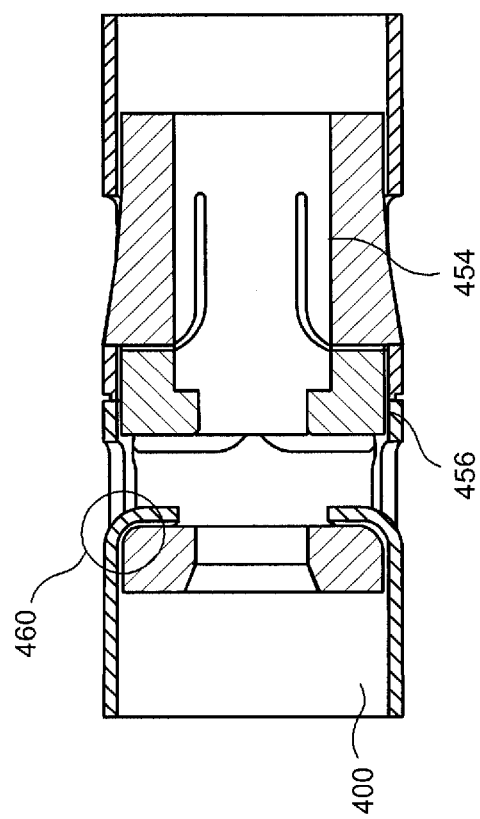
FIG. 24 is a diagram showing a detail of a second embodiment of the interlock tube shown in FIG. 19.

In a second embodiment shown in FIGS. 19, 23 and 24, the interlock tube 454 comprises a portion 456 at locations where the proximal tabs 412 bend. The portion 456 may comprise a rounded edge 460, shown in FIG. 23, or a squared off edge 458 shown in FIG. 24. Those skilled in the art will understand that the edge conditions of the interlock tube 454 help control the force required to pull in and unbend the tabs with square ended tabs requiring a greater pulling force than tabs with rounded edges. Another embodiment according to the invention, as shown in FIG. 20, comprises an interlock tube 462 with a portion 464 forming the bend of the tabs 412 at the proximal end of the capsule 400, rather than at the distal end.

Figure 21:
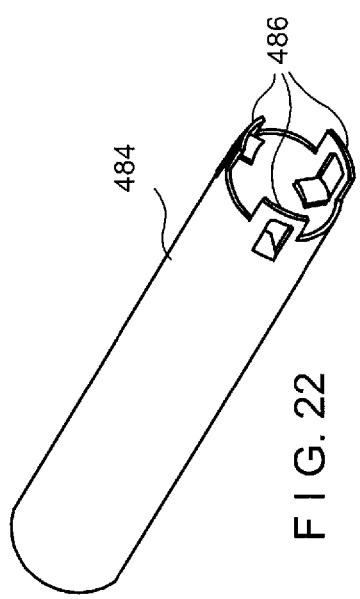
FIG. 21 is a diagram showing an exemplary embodiment of a tab configuration for a capsule.
Figure 22:
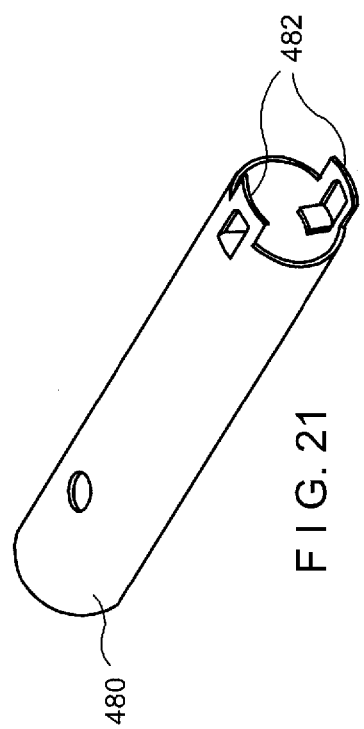
FIG. 22 is a diagram showing a second exemplary embodiment of a tab configuration for a capsule.

Further exemplary embodiments of the present invention may comprise different configurations of the tabs. The configuration may be varied to obtain a desired separation force of the components. For example, FIG. 21 shows a capsule 480 comprising a pair of tabs 482. In another example shown in FIG. 22, the capsule 484 comprises three tabs 486, that may be placed equidistantly around the body of the capsule 484. It will be understood by those of skill in the art that the number and configuration of the tabs at the proximal and the distal end of the capsule may be selected to obtain a desired separation force.

Figure 25:
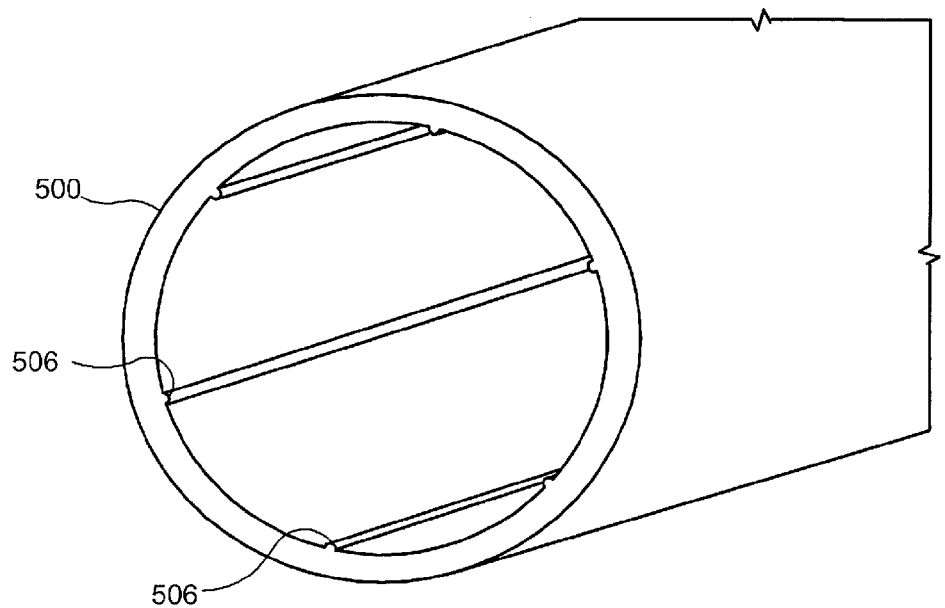
FIG. 25 is a diagram showing a first embodiment of a channel protector according to the invention.

Components of the hemostatic clip delivery system have sharp edges that can easily damage the working channel of the endoscope. It is thus beneficial to guard against such damage by using protective coatings or sheaths over the outer surfaces of the clip delivery system. FIG. 25 shows an exemplary embodiment of an endoscope protective system including a reduced contact sheath 500 slid over the entire length of the clip delivery system from the distal end of the clip at least to the point at which the flexible member 130 enters the working channel of the scope to shield inner surfaces of the endoscope working channel from sharp or jagged edges of the components of the system. As would be understood by those skilled in the art, the sheath 500 may be manufactured from any of a variety of suitable plastic materials. After the capsule has been passed through the endoscope, the sheath 500 is withdrawn to expose the clip for use. Ridges or bumps 506 may be formed on an inner diameter of the sheath 500 to reduce contact friction between the sheath 500 and the clip deployment device.

Figure 26:
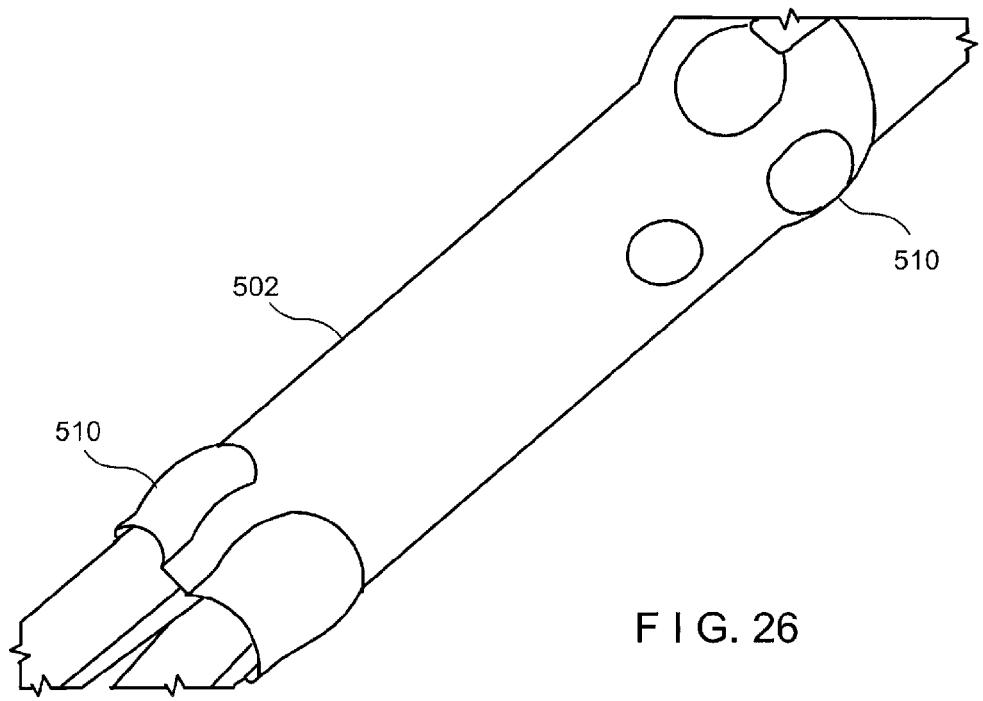
FIG. 26 is a diagram showing a second embodiment of a channel protector.

As shown in FIG. 26, in a different embodiment, protrusions 510 may be formed on an outer surface of the capsule 502 and/or of the bushing 404 of FIGS. 17-20 to generate a clearance between selected portions of the outer surface 502 and an inner surface of the working channel to protect either or both of the working channel and these selected portions by preventing contact therebetween. These protrusions may comprise bumps, ridges, rings or any other shape having a height sufficient to extend beyond the sharp points of the device, thus keeping them away from the walls of the endoscope working channel. The protrusions 510 may be stamped, machined or deposited as an adhesive on the device as would be understood by those skilled in the art. FIG. 27 shows a protective skirt 514 formed as a heat shrink or other protective coating covering all or selected portions of the components of the system to prevent contact between sharp edges of the clip deployment device 512 and the endoscope working channel. The skirt 514 may be formed of any material, preferably a polymer, that adheres to metal.

FIG. 28 shows a clip deployment device 520 comprising a plastic helmet 522 encapsulating the entire distal tip of the device 520. The helmet 522 may, for example, be formed of two parts 524, 526 kept together while passing through the endoscope working channel but which is pushed off the distal end of the device 520 as the clip 102 is advanced out of the capsule 110 and the arms 104 separate from one another.

Figure 29:
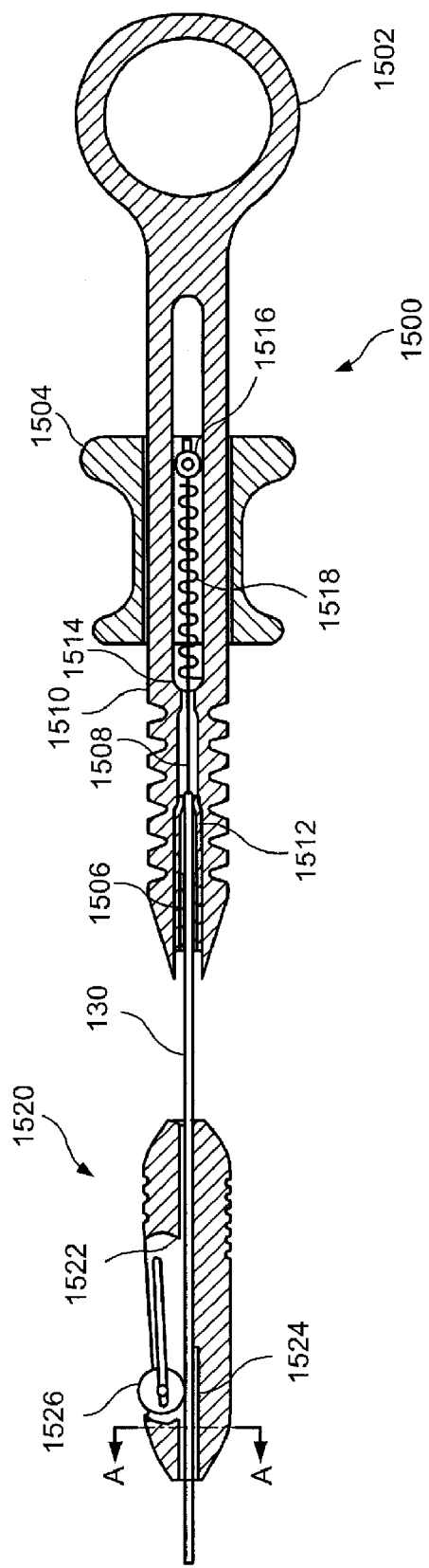
FIG. 29 is a cross sectional view of a handle including a rotating actuator for use with a device according to an embodiment of the invention.
Figure 30:
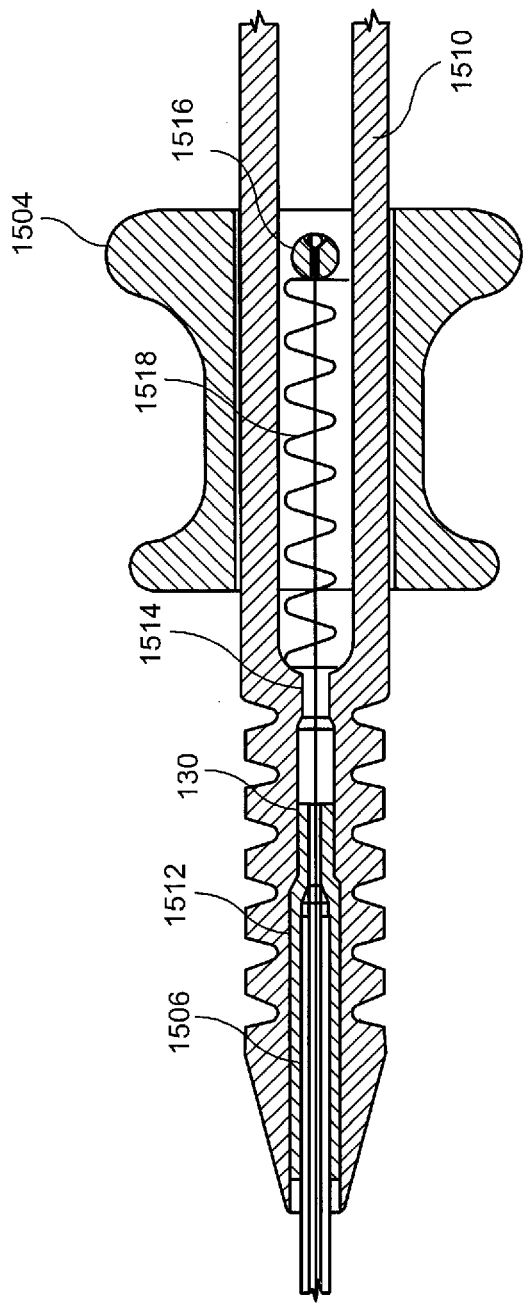
FIG. 30 is a close up of a distal portion of the cross sectional view of FIG. 29.

As shown in FIG. 29, according to one embodiment of the present invention, a handle 1500 of a device, such as the device 100, includes a body 1510 with a thumb ring 1502 rigidly coupled thereto. The body 1510 is rigidly coupled to the flexible member 130 as described in more detail below. In addition a spool 1504 is slidably coupled to the body 1510 and rigidly coupled to the control wire 132 so that actuating the thumb ring 1502 (i.e., moving the thumb ring 1502 proximally and distally relative to the spool 1504) moves the flexible member 130 proximally and distally relative to the control wire 132. For example, as shown in FIGS. 29 and 30, the flexible member 130 is rigidly coupled to the handle 1500 via a barb stop component 1506 mounted within an inner lumen 1508 of a distal extension 1510 of the thumb ring 1502. The barb stop component 1506 is preferably formed as a cylinder with an inner diameter greater than an outer diameter of the flexible member 130. According to an alternative embodiment of the present invention, a barb 1512 or other abutting surface (e.g., a crimp band) extending radially outward from the flexible member 130 proximally of the proximal end of the barb stop component 1506 limits travel of the flexible member distally relative to the handle 1500 while a reduced diameter section 1514 of the lumen 1508 limits travel of the flexible member 130 proximally relative to the handle 1500. Thus, the flexible member 130 may be advanced or retracted by manipulating the handle 1500. The control wire 132 extends proximally past the reduced diameter section 1514 to a socket 1516 coupled to the spool 1504 so that movement of the thumb ring 1502 proximally and distally relative to the spool 1504 generates a corresponding movement of the control wire 132 relative to the flexible member 130 to actuate the clip 102 as desired. A spring 1518 mounted between the socket 1516 and a proximal face of the reduced diameter section 1514 biases the spool 1504 and the thumb ring 1502 toward a desired resting position.

Figure 31:
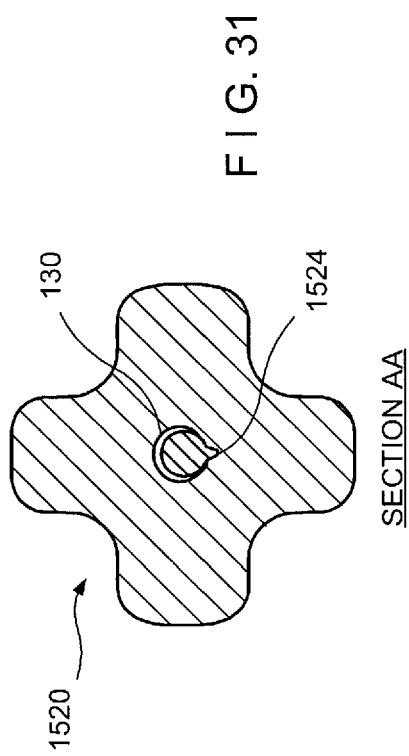
FIG. 31 is a cross section along line A-A of FIG. 29.

In addition, as shown in FIGS. 29 and 31, the handle 1500 may optionally include an adjustable rotation actuator 1520 which may be moved along the flexible member 130 to assist in rotating the member 130 and the clip 102 as desired. For example, a lumen 1522 extending through the adjustable rotation actuator 1520 includes a locking portion 1524 including surfaces shaped so that, when the flexible member 130 is pushed thereagainst, the actuator 1520 is locked to the flexible member 130 so that rotation of the actuator 1520 rotates the flexible member 130. As would be understood by those skilled in the art, the surfaces of the locking portion 1524 may form a V into which the flexible member may be urged to lock the actuator 1520 to the flexible member 130. The actuator 1520 also includes a locking member 1526 moveable into and out of engagement with the flexible member 130 to lock and unlock the flexible member 130 and the actuator 1520. Thus, when the locking member 1526 is out of engagement with the flexible member 130 (i.e., when rotated away from the locking portion 1524), the actuator 1520 may be slid along the flexible member 130 to any desired point and, in this condition, rotation of the actuator 1520 does not rotate the flexible member 130.

Alternatively, as would be understood by those skilled in the art, the clip 102 may be rotated via a control wire 132 rigidly coupled to a rotation actuator of a handle and to the clip 102. This control wire 132 would rotate within the flexible member 130 which would be rigidly coupled to a portion of the handle rotatable relative to the rotation actuator. In this case, the bushing 120 would be rotatably coupled to the distal end of the flexible member 130 while the couplings between the handle, the control wire 132 and the flexible member 130 would be similar to those described above for the handle 1500 except that the control wire 132 would be rotating relative to the flexible member 130.

FIG. 32 shows a proximal end of a capsule 1110 according to an alternate embodiment of the invention. The capsule 1110 may be substantially identical to the capsule 110 except as specifically pointed out below and will interact with the rest of the apparatus of FIG. 1 in substantially the same manner as that described for capsule 110. The slot 152 of capsule 110 has been split in two pieces in the capsule 1110 of FIG. 32 with a pair of distal slots 1152 receiving the tabs 150 of the clip 102 and a pair of proximal slots 1153 receiving the tabs 156 of the bushing 120. Between each of the slots 1152 and the corresponding slot 1153 is a protrusion 1154 which ensures that a clearance is maintained between ends of the tabs 150 and 156 and an inner surface of a working channel within which the capsule 1110 is moved. That is, the protrusions 1154 ensure that ends of the tabs 150, 156 do not project outward beyond a profile of the capsule 1110. Similarly, as shown in FIGS. 33 and 34, a capsule 1120 includes a pair of first slots 1162 receiving the tabs 150 of the clip 102 and a second pair of slots 1164 for receiving the tabs 156 of the bushing 120. In the capsule 1120, the slots 1164 are covered by a ramp 1166 which serves the same purpose as the protrusions of the capsule 1110 while also covering the slots 1164 to further prevent contact between the tabs 156 and any external surfaces.

Figure 35:
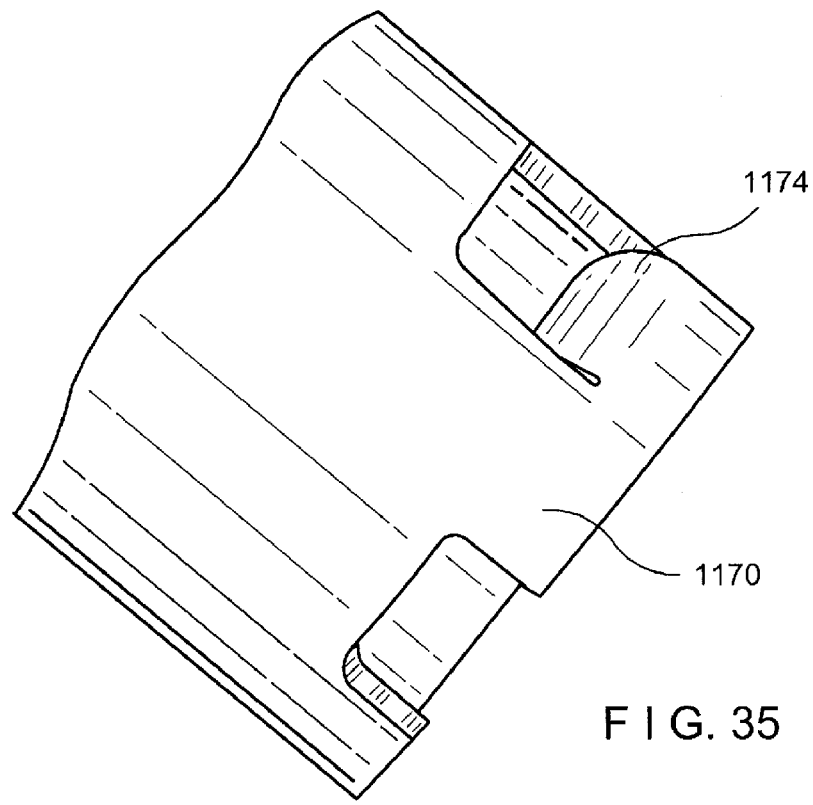
FIG. 35 is a perspective view of a still further alternate capsule for use with the apparatus of FIG. 1.
Figure 36:
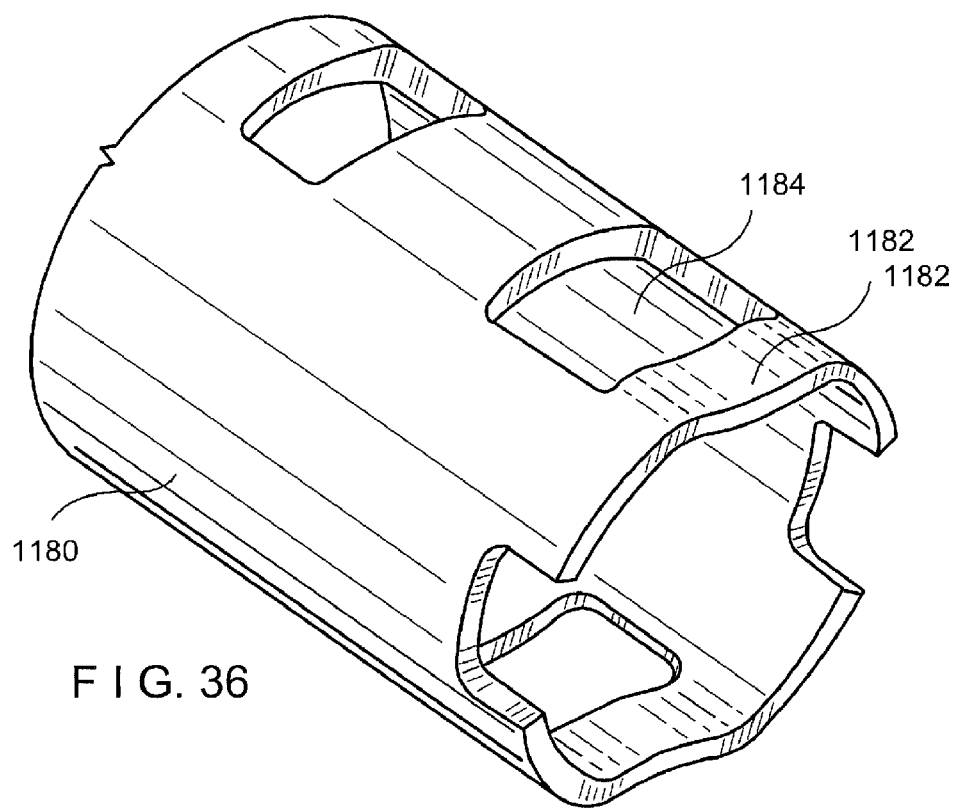
FIG. 36 is a perspective view of another alternate capsule for use with the apparatus of FIG. 1.
Figure 38:
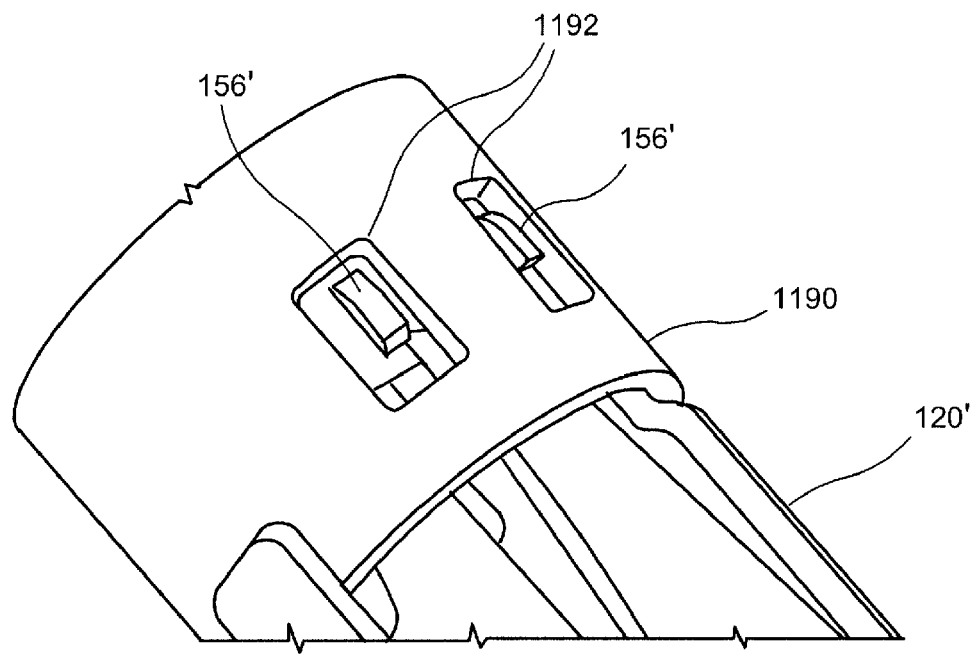
FIG. 38 is a perspective view of another alternate capsule for use with the apparatus of FIG. 1.
Figure 39:
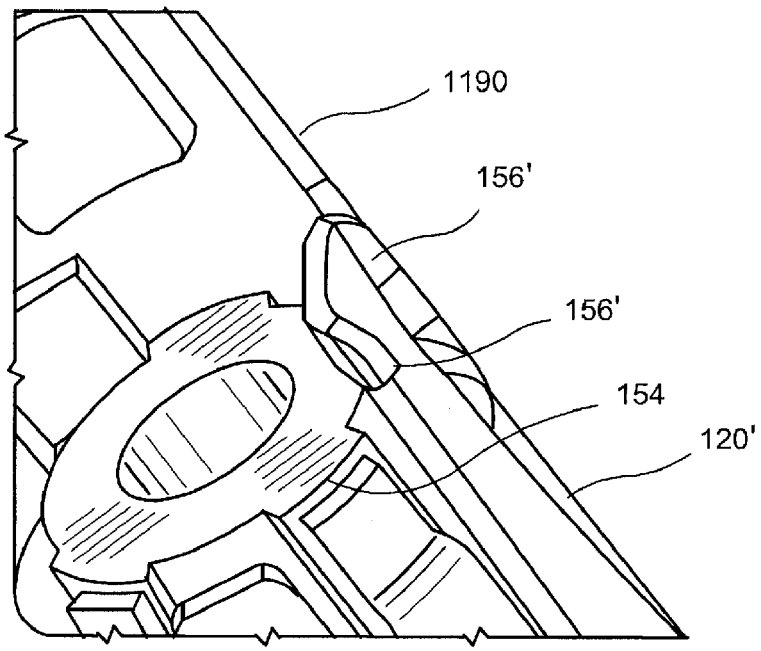
FIG. 39 is a perspective view of a proximal end of the capsule of FIG. 38.
Figure 42:
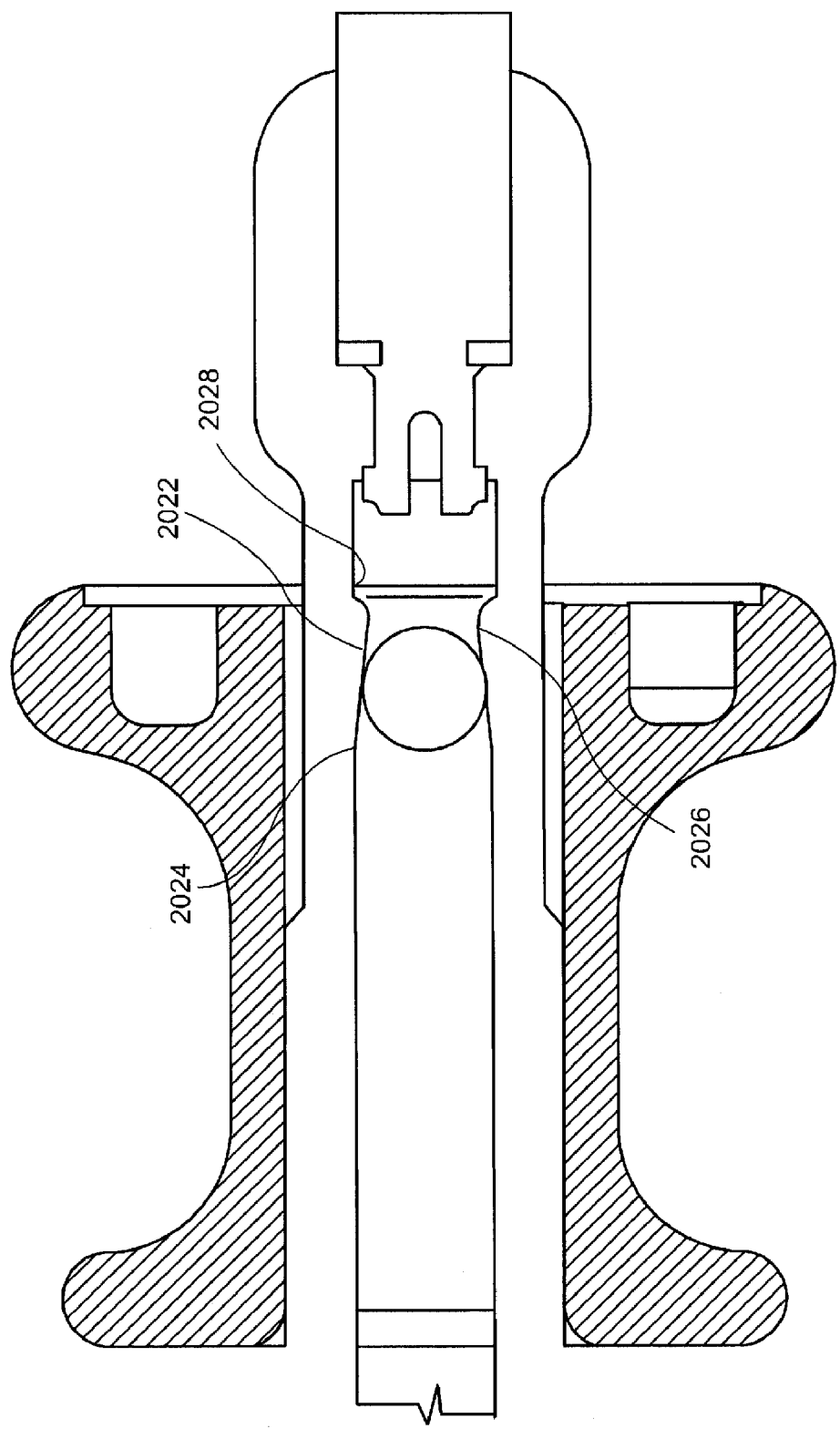
FIG. 42 is a cross-sectional side view of the handle of FIG. 40 in a pre-locked state.
Figure 43:
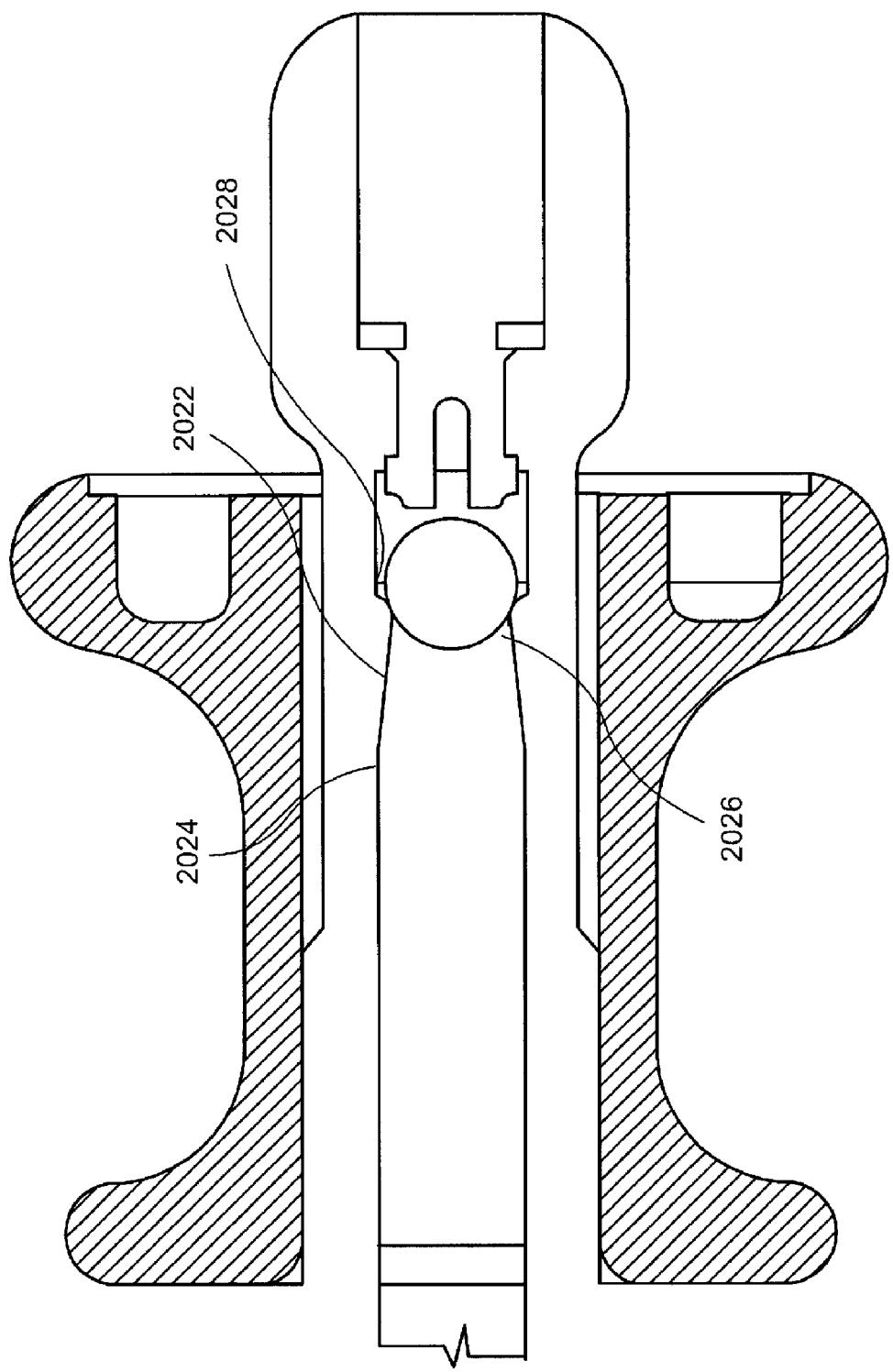
FIG. 43 is a cross-sectional side view of the handle of FIG. 40 in a locked state.

A similar purpose is served in capsule 1170 of FIG. 35 by tabs 1170 extending into slots 1174 radially inward to form a surface for engaging the tabs 156 of the bushing 120 at a point radially within an outer diameter of the capsule 1170. Similarly, as shown in FIGS. 36 and 37, a capsule 1180 includes concave indentations 1182 in surfaces at the proximal ends of slots 1184 receiving the tabs 156 of the bushing 120 will maintain ends of the tabs 156 further radially inward preventing contact between the tabs 156 and any external surfaces. Finally, as shown in FIGS. 38 and 39, a capsule 1190 includes a first pair of slots 1192 receiving a corresponding pair of tab ends 156' and a second pair of slots 1192 at a radially opposite location receiving a second pair of tab ends 156' (not shown). Each of the tab ends 156' extends from a lateral end of a tabs of a bushing 120' and includes a rounded, laterally shortened face abutting a proximal end surface of the corresponding slot 1192 with the tab ends 156' remaining within an outer diameter of the capsule 1190.

The present invention has been described with reference to specific exemplary embodiments. Those skilled in the art will understand that changes may be made in details, particularly in matters of shape, size, material and arrangement of parts without departing from the teachings of the invention. For example, clips as described above may be incorporated in a multi-clip dispensing system so that multiple areas may be clipped without removing the device from the body. As described above, the use of a bent distal portion of a control wire would allow for one or more distal clips to be deployed while still retaining one or more proximal clips. After each clip deployment, the bent distal portion of the control wire may recover to its bent state. In addition, any of the clips according to the present invention may be selectively energized (e.g., by connection to a source of heat or RF or laser energy) to ablate or cauterize tissue, as would be understood by those skilled in the art.

FIGS. 40-43 show an exemplary embodiment of a handle 2000 for use with a device according to the invention such as the device 100 described above. Although the handle 2000 will be described in conjunction with the device 100, those skilled in the art will understand that this handle 2000 may be employed with any of the various devices described herein. The handle 2000 includes a body 2010 rigidly coupled to the flexible member 130 and a thumb ring 2012 rotatably mounted at a proximal end thereof. A slide member 2014 is mounted to the body by means of a pin 2016 slidably received in a slide channel 2018. The pin 2016 may then be mounted to a proximal end of the control wire 132 so that movement of the slide member 2014 proximally and distally relative to the body 2010 moves the control wire 132 proximally and distally relative to the flexible member 130 to operate the device 100 as described above. Furthermore, rotation of the slide member 2014 and the body 2010 relative to the thumb ring 2012 rotates the clip 102 obviating the need for the rotation actuator of the embodiment of FIGS. 29 and 31.

In addition, the proximal end of the slide channel 2018 includes a locking structure 2020 which, in the embodiment of FIGS. 40-43 is formed as a tapered section 2022 of the slide channel 2018. The tapered section 2022 includes opposed arms 2023 each of which necks inward toward the center of the slide channel 2018 as it progresses from a distal end 2024 toward a proximal end 2026 which forms a proximally-facing shoulder 2028. As the slide member 2014 is moved proximally through the slide channel 2018 and the pin 2016 moves into the tapered section 2022, contact between the opposed arms 2023 and the pin 2016 provides resistance to further proximal movement of the slide member 2014 which gradually increases until the pin 2016 moves proximally past the proximal ends 2026. At this point the arms 2023 which had been moved radially outward during the passage of the pin 2016 therethrough, spring back under natural bias and the slide member 2014 is permanently locked in a proximal position by contact between the pin 2016 and the shoulders 2028. The position of the shoulders 2028 is selected so that, when the slide 2014 reaches the proximal position, the clip 102 is locked closed and has been separated from the distal end of the control wire 132 with the severed distal end of the control wire 132 locked within the bushing 120. This prevents any distal movement of the control wire 132 after the capsule 110 has been separated from the bushing 120 avoiding any damage to surrounding tissue that might result if the severed end of the control wire 132 were to be extended out of the bushing 120. In addition, preventing such distal movement of the control wire 132 eliminates the possibility that the bushing support 154 may be pushed by the constraint tube 140 back into the bushing 120 relocking the capsule 110 to the bushing 120.

A handle according to a further embodiment of the invention may be substantially similar to the handle 2000 except for the construction of a body 2010' as shown in FIGS. 44 and 45. The body 2010' is substantially the same as the body 2010 except that arms 2023' of the tapered section 2022' are formed as cut-outs from an outer wall 2030' of the handle 2010'. That is, the arms 2023' extend from distal ends 2024' coupled to the wall 2030' along an arc to proximal ends 2026' which are cantilevered out from the wall 2030' and which extend into the slide channel 2018'. As with the body 2010, the distal ends 2024' of the arms 2023' form proximally facing shoulders 2028' so that, when the pin 2016 has been moved proximally therepast, the arms 2023' spring back toward the center of the slide channel 2018' with the shoulders 2028' contacting the pin 2016 and preventing movement of the pin 2016 distally therepast in the same manner described above.

Figure 46:
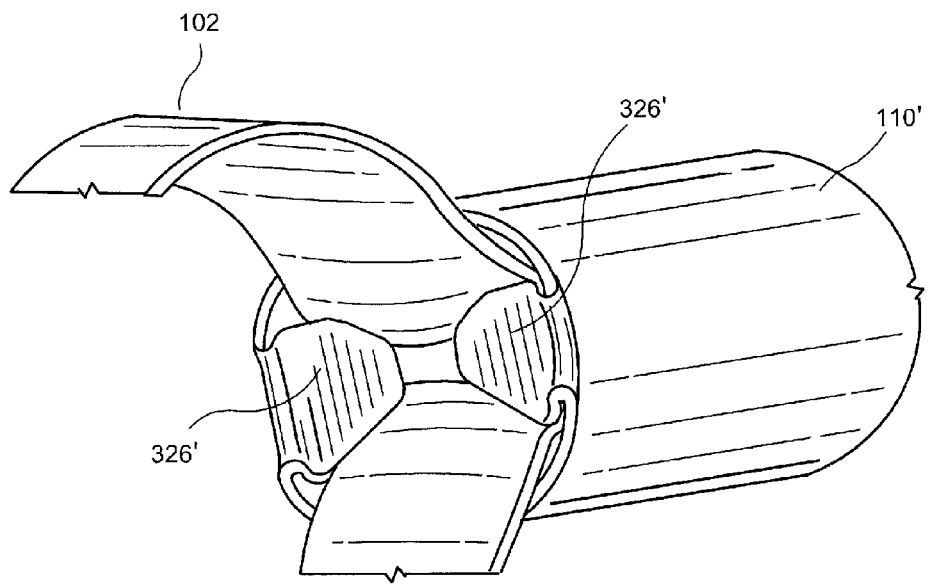
FIG. 46 is a perspective view of still another alternate capsule for use with the apparatus of FIG. 1.

FIGS. 46-51 show various apparatus for constraining motion of a clip according to the present invention. Although the embodiments shown in FIGS. 46-51 will be described in conjunction with the device 100, those skilled in the art will understand that they may be employed with any of the various devices described herein. As shown in FIG. 46, the capsule 110' comprises distal tabs 326' which may be substantially similar to the tabs 326 except that the tabs 326' are bent inwards at an angle greater than 90° toward a centerline of the capsule 100. That is, ends of the tabs 326' are bent into the capsule 110' until distal ends of the tabs 326' are located further proximally than the distal end of the capsule 110'. Similar to the tabs 326, the tabs 326' hold the clip 102 in position, limiting rotation of the clip 102 about the longitudinal axis of the capsule 110' and functioning as cams that force the arms 104 of the clip 102 open as the clip 102 is moved distally out of the capsule 110'. Because the ends of the tabs 326' are located further proximally than are the ends of the tabs 326, the distal-most position of the clip 102 is more proximal in this embodiment than in the capsule 110. That is, the point at which the clip 102 can be advanced no further distally due to contact between the cross bar 134 and the tabs 326' or a portion of the clip 102 which cannot spread further apart is further proximally than with the clip 102 and the tabs 326. This predetermined distance may be varied by adjusting the angle of the tabs 326'. The angle may range between 90° and 180°, where an increase in the angle causes the tabs 326' to stop distal advancement of the clip 102 sooner (i.e., the predetermined distance increases with the angle of the tabs 326'). Thus, the tabs 326' define a distal-most position of the clip 102.

Figure 47:
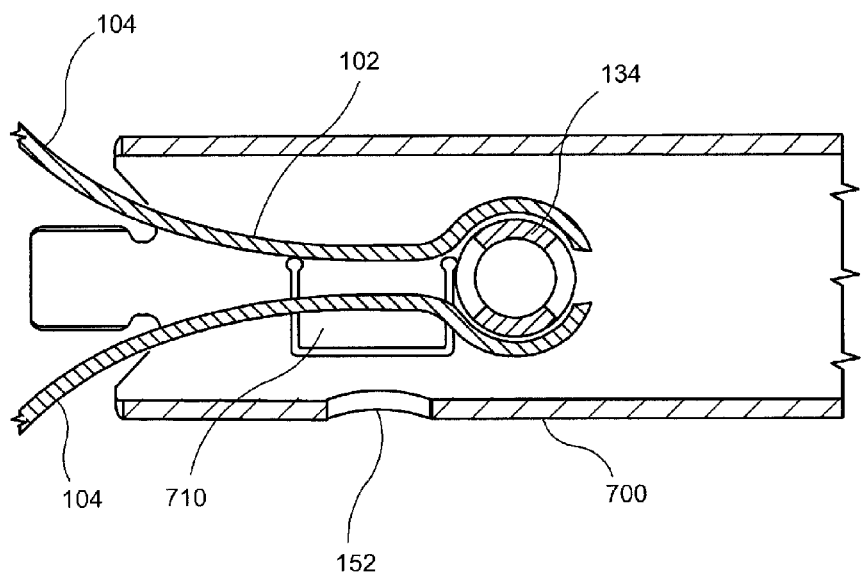
FIG. 47 is a cross-sectional side view of a distal portion of another alternate capsule for use with the apparatus of FIG. 1.

FIG. 47 shows a capsule 700 according to an exemplary embodiment of the present invention. The capsule 700 includes a limiting tab 710 disposed along a wall thereof. The tab 710 may be formed by cutting into the wall of the capsule 700 to form a windowed flap. During an assembly process, the tab 710 may be pushed inward toward the longitudinal axis of the capsule 700 (e.g., using a finger or a crimping tool) to form a limiting structure radially positioned between top and bottom portions of the clip 102 (e.g., between the arms 104). The tab 710 is disposed between the distal and proximal ends of the clip 102, allowing the clip 102 to be distally advanced until the cross bar 134 reaches the tab 710. As would be understood by those skilled in the art, the material from which the capsule 700 is formed (e.g., stainless steel, titanium, etc.) is sufficiently pliable so as to allow the inward bending of the tab 710 and the size of the tab is selected to be resilient enough to resist deformation when pressure is exerted against the tab 710 by the cross bar 134. Thus, the tab 710 defines a distal-most position of the clip 102. Sides of the tab 710 may also be bent or cut at an angle or curved to facilitate camming of the arms 104. For example the tab 710 may be bent to form a ramp extending at angle towards the distal end of the capsule 700.

Figure 48:
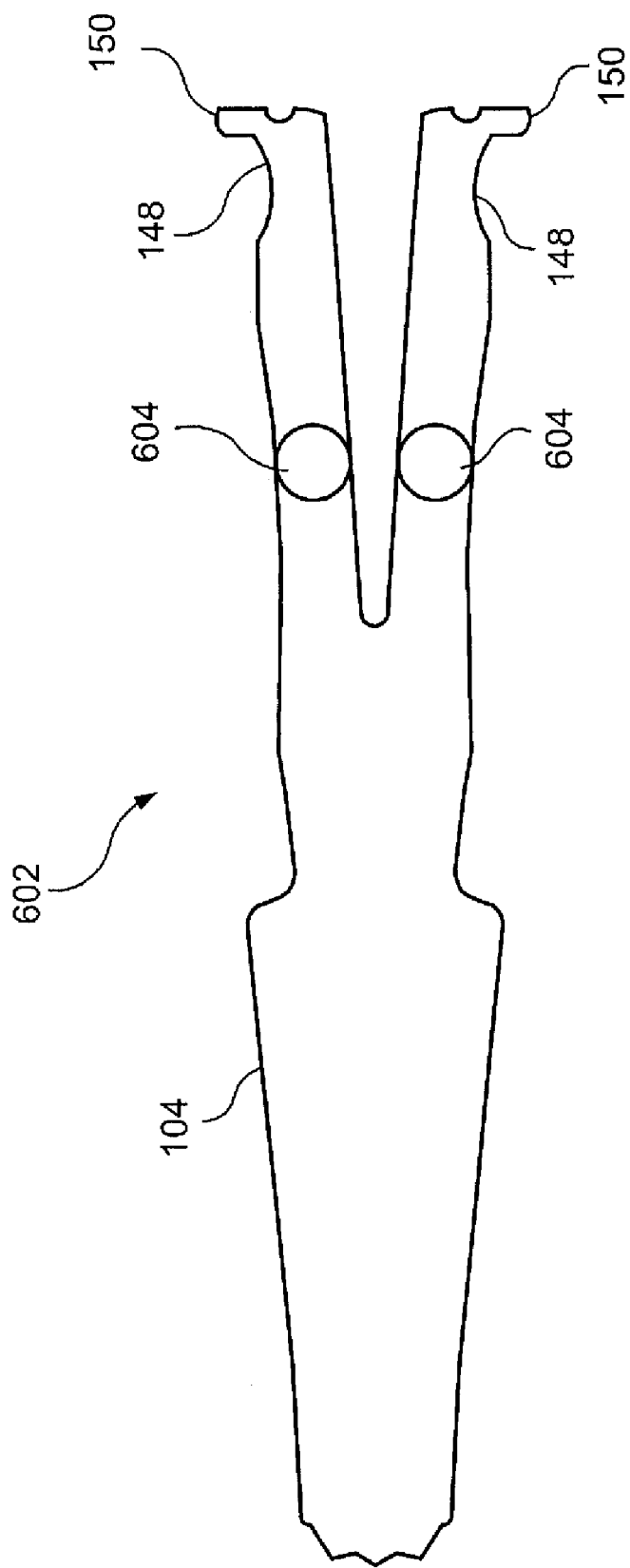
FIG. 48 is a top view of an alternate single piece clip for use with the apparatus of FIG. 1.

FIG. 48 shows a top view of an exemplary embodiment of a clip 602 including features substantially similar to those of the clip 102, such as a pair of distally located arms 104 and proximal tabs 150. The clip 602 operates substantially similarly to the clip 102 described above except that it also includes one or more points 604 at which top and bottom portions of the clip 602 are joined together (e.g., by welding, soldering, riveting, etc.). The points 604 are disposed distally of the cross bar 134 and therefore engage the distal tabs of a capsule (e.g., tabs 326 of the capsule 110) or limit the extent to which the arms 104 can spread when the clip 602 is distally advanced to limit distal advancement and opening of the clip 602.

Figure 49:
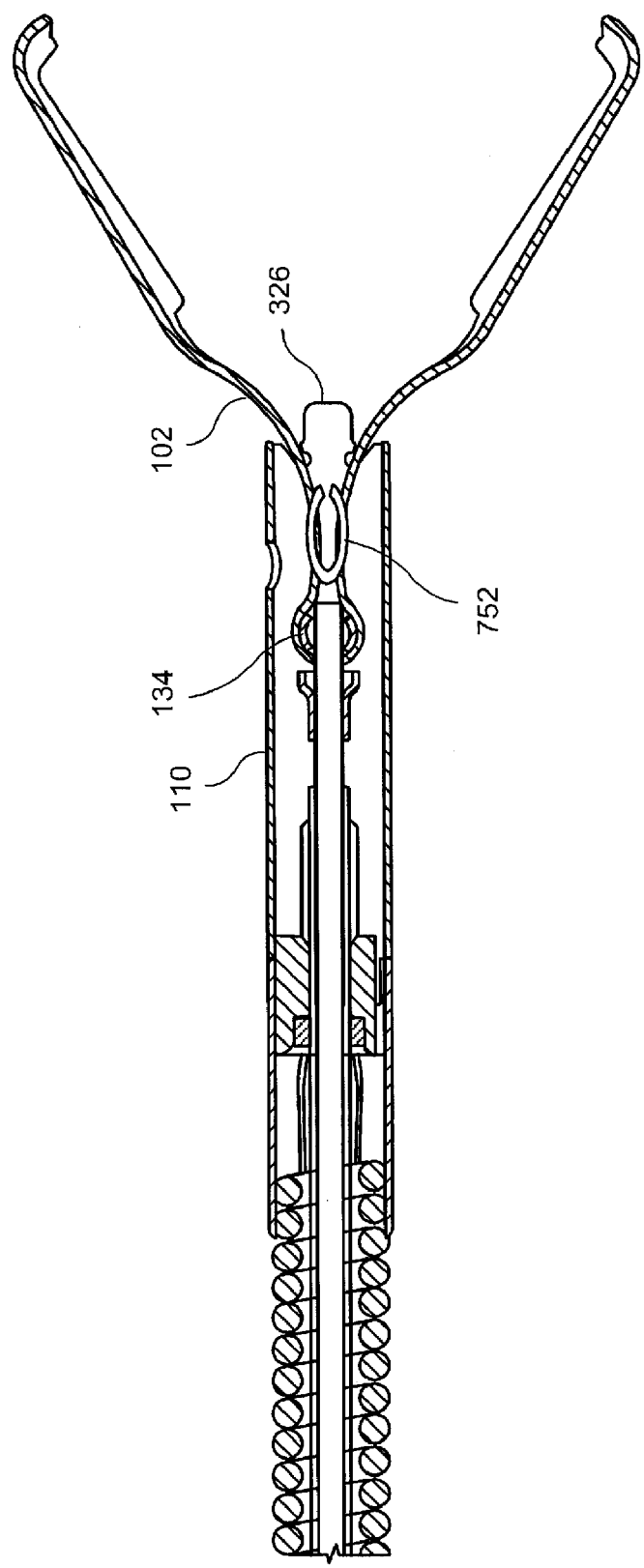
FIG. 49 shows an embodiment of a capsule insert for use with the apparatus of FIG. 1.

FIG. 49 shows an embodiment of an insert 752 located between the arms 104 of the clip 102 proximally of the tabs 326. The insert 752 may be formed, for example, of a hard plastic or other substantially rigid material and comprises a substantially elliptical or oval cross-section to facilitate placement of the insert 752 between the arms 104. However, those skilled in the art will understand that other shapes may be utilized so long as the insert provides the desired limit in distal travel of the clip relative to the capsule. The insert 752 is free-floating between the arms 104 and contacts the tabs 326 to limit distal advancement of the clip 102. As the clip 102 advances, the insert 752 engages the tabs 326 and is pushed proximally until a proximal end thereof contacts the cross bar 134 defining a distal-most position of the clip 102 which may be adjusted by changing the size of the insert 752.

Figure 50:
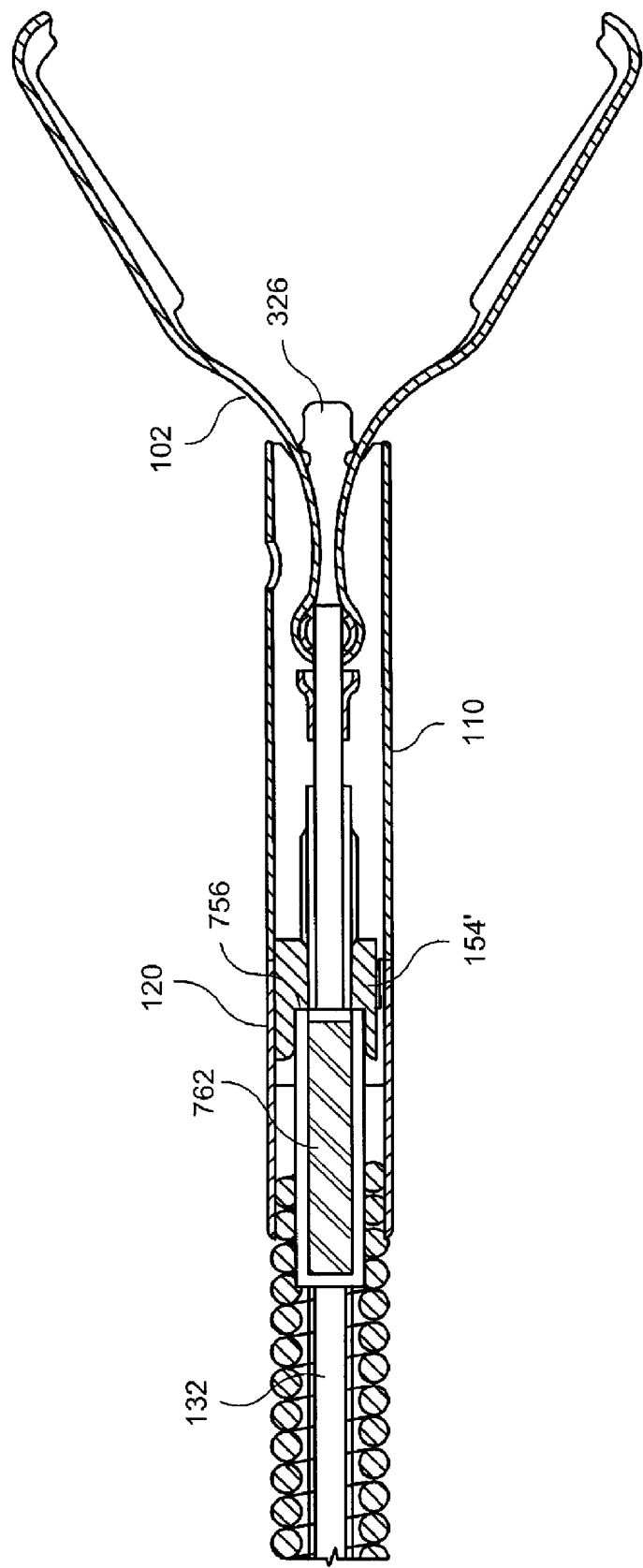
FIG. 50 is a side view of an exemplary embodiment of an arrangement for limiting the extent to which the clip can be opened.

FIG. 50 shows an exemplary embodiment of a bushing arrangement in which the clipping device 100 includes an increased diameter portion 762 of the control wire 132 extending proximally of a proximal end of the bushing support 154'. The increased diameter portion 762 of the control wire 132 may be formed, for example, by attaching a hypotube or other structure around a desired portion of the control wire 132 by, for example, welding or crimping. The portion 762 is positioned so that, when the clip 102 is in a desired distal-most position, the distal end of the portion 762 abuts a shoulder 756 formed at a proximal end of the bushing support 154' preventing further distal movement of the control wire 132 and, consequently, of the clip 102. The bushing support 154' itself is prevented from moving distally by the tabs 156 which lock the bushing 120 to the capsule 110. Thus, a distal-most position of the control wire 132 and the clip 102 is defined by the distal end of the pocket 756. In an alternative embodiment, a stopping member (e.g., a cylindrical wedge or washer) may be placed anywhere along the length of the bushing 120 to stop the portion 762. A diameter of an opening of the stopping member is sized to allow the control wire 132 to pass through while stopping the portion 762.

Figure 51:
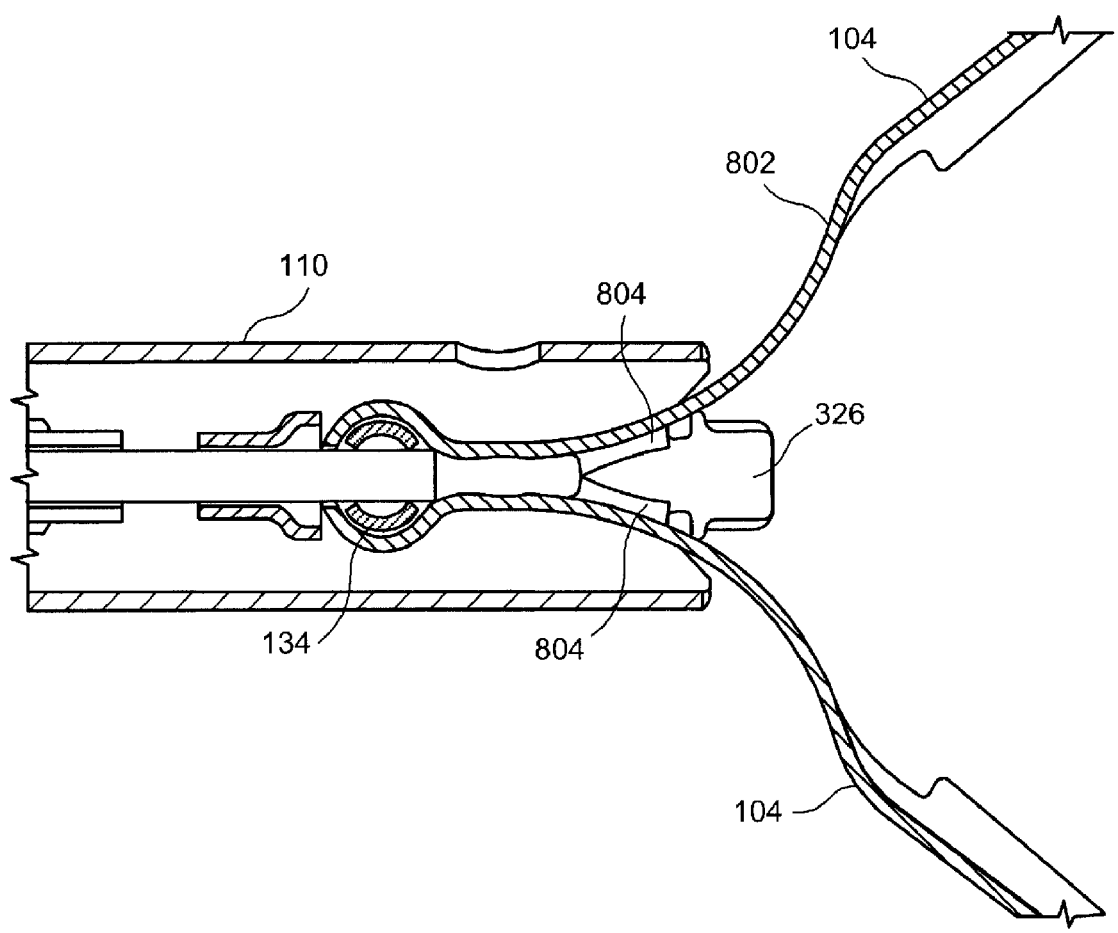
FIG. 51 is a side view of a further alternate single piece clip for use with the apparatus of FIG. 1.

FIG. 51 shows an exemplary embodiment of a clip 802 that includes tabs 804 disposed along top and bottom portions thereof between the cross bar 134 and the arms 104. The tabs 804 are formed by bending innermost edges of the laterally separated portions 148 toward a central axis of the clip 802. The tabs 804 may be formed during a manufacturing process in which the proximal end of the clip 802 is split to form the separated portions 148. The tabs 804 engage the distal tabs 326 of the capsule 110 as the clip 102 is distally advanced, forming a positive stop that prevents further distal movement of the clip 102. In addition, proximal ends of the tabs 804 are positioned in proximity to one another to limit opening of the arms 104. As the arms 104 open, the proximal ends engage one another to resist further opening. After the arms 104 are closed, the tabs 804 interlock to assist in maintaining the clip 102 in a closed configuration.

In addition to the embodiments described, a size of any of the clips according to the invention may be selected depending on the application for the clip is designed. Clips according to the present invention may be designed in a wide variety of sizes for applications such as wound closure, hemostasis, tissue bunching (e.g., to alter the size of shape of a hollow organ). Alternatively clips according to the present invention may be used to anchor items to tissue. As would be understood by those skilled in the art, clips for wound closure may come in a wide variety of sizes depending on the size of the wounds for which they are intended. For example, wound closure clips may range in size from 0.25 mm to 25 mm in diameter while hemostasis clips may have an extensive range of size, wherein the size of the hemostasis clip may vary based on the size of the bleeding anatomy However, those skilled in the art will understand that other sizes may be employed depending on the anatomy of the area to be treated. Furthermore, the clips according to the present invention are preferably formed of biocompatible materials such as metals, polymers, ceramics, biologicals and/or combinations thereof. The clips may be selected based on the requirements of particular applications to biodegrade, bioabsorb, pass out of the body naturally or be removed therefrom as would be understood by those skilled in the art. Accordingly, various modifications and changes may be made to the embodiments without departing from the broadest scope of the invention as set forth in the claims that follow. The specifications and drawings are, therefore, to be regarded in an illustrative rather than a restrictive sense.

What is claimed is:

1. A tissue clipping apparatus, comprising:
   a clip including a proximal end received within a capsule, the clip including a clip locking member biased to engage a first locking structure of the capsule to lock the clip in the capsule in a closed configuration; and
   a tension member releasably coupling the clip to a proximal end of the apparatus which, during use, remains accessible to a user, the tension member being coupled to the clip by a joint designed to release when subject to a predetermined load to separate the clip from the apparatus, release of the joint releasing the locking member to engage the first locking structure;
   a constraint member coupled to the tension member and releasably connected to the clip, wherein when coupled to the clip, the constraint member maintains the locking member of the clip out of engagement with the first locking structure of the capsule, release of the joint allowing the constraint member to move to a release position releasing the locking member to engage the first locking structure;

a proximal member extending from the proximal end of the apparatus to releasably couple to the capsule, a distal end of the proximal member comprising a bushing releasably coupled to the capsule, the bushing comprising a bushing locking feature biased toward an unlocked position and a support received within the bushing to urge the bushing locking feature into engagement with a second locking structure of the capsule.

2. The apparatus according to claim 1, wherein after moving to the release position, the constraint member displaces the support from the bushing disengaging the bushing locking feature from the second locking structure of the capsule.

3. The apparatus according to claim 1, wherein a single opening in the capsule forms the first and second locking structures and so that the clip locking member comprises a tab aligned with the opening.

4. The apparatus according to claim 1, wherein the joint includes a coupling member welded to the tension member.

5. The apparatus according to claim 4, wherein the coupling member comprises a cross bar welded to the tension member.

6. The apparatus according to claim 5, wherein a proximal end of the clip defines a space sized for retaining the coupling member.

7. The apparatus according to claim 1, wherein the clip comprises proximal slots for receiving distal tabs of the constraint member.

8. The apparatus according to claim 1, wherein the tension member comprises a wire with the joint comprising a curved portion of the wire received in a corresponding space of the clip, the curved portion straightening when subject to the predetermined load to release the wire from the clip.

9. The apparatus according to claim 1, wherein the capsule comprises a tab bent into an interior of the capsule to hold the clip before deployment and to cam arms thereof open during deployment.

10. The apparatus according to claim 1, wherein the bushing locking feature comprises a tab biased toward a centerline of the bushing and wherein the second locking structure of the capsule comprises an opening into which the support urges the tab.

11. The apparatus according to claim 10, wherein the tab comprises bent ears increasing engagement force with the support.

12. The apparatus according to claim 1, wherein the capsule includes a groove mating with a corresponding feature of the bushing to align the capsule with the bushing.

13. The apparatus according to claim 1, wherein a surface of the support mating with the bushing includes one of a shelf, a groove, a smooth surface, a pocket and an undercut.

14. The apparatus according to claim 1, further comprising:

a scope channel protector preventing contact between selected portions of the apparatus and a scope into which the apparatus is inserted.

15. The apparatus according to claim 14, wherein the scope channel protector is one of a reduced contact sheath, a protrusion, a heat shrink skirt and a helmet.

16. The apparatus according to claim 1, further comprising:

a handle and a slide member coupled to the tension member so that movement of the slide member relative to the handle applies tension to the clip via the tension member.

17. The apparatus according to claim 16, wherein the handle further comprise a lockout mechanism preventing distal actuation of the tension member after the capsule has been separated from the bushing.

18. The apparatus according to claim 17, wherein the handle includes a slide member coupled to the tension member and slidable relative to a body of the handle, the lockout mechanism including a proximal stop preventing distal movement of the slide member therepast after the slide member has been moved proximally past the proximal stop.

19. A clip delivery apparatus, comprising:

a flexible member sized for insertion through a working channel of an endoscope to a target site within a body and a capsule releasably coupled to a distal end of the flexible member, in combination with a clip, a proximal end of which is received within the capsule and a tension member extending through the flexible member to a proximal end of the clip; and a binding member coupling the tension member to the clip, a connection between the binding member and the tension member yielding when subject to a predetermined load and a constraint member maintaining the clip in an unlocked configuration, the constraint member being coupled to the tension member and releasably connected to the clip so that, when the connection between the binding member and the tension member yields, the constraint member releases from the clip allowing the clip to move to a locked configuration in which the clip is locked closed;

a bushing releasably connecting a distal end of the flexible member and the capsule;

an interlock tube in an interference fit between the capsule and the bushing;

wherein the tension member includes an abutting surface which, after the connection between the tension member and the binding member yields, pushes the interlock tube into the bushing separating the capsule from the bushing.

20. The apparatus according to claim 19, wherein the interlock tube is pushed into the bushing, it displaces a first tab of the capsule from a corresponding window of the bushing.

21. The apparatus according to claim 20, wherein a proximal end of the capsule includes a second tab engaging an abutting surface of the interlock tube.

22. The apparatus according to claim 21, wherein the abutting surface is a side of a recess formed in the interlock tube, an interface between the abutting surface and an outer surface of the interlock tube including one of a rounded edge and a squared off surface.

23. The apparatus according to claim 19, further comprising:

a scope channel protector preventing contact between at least sharp portions of the apparatus and an inner surface of a working channel of an endoscope through which the apparatus is inserted into the body.

24. The apparatus according to claim 23, wherein the scope channel protector is one of a reduced contact sheath, a protrusion, a heat shrink skirt and a helmet.

* * * * *